(12) United States Patent
Krieger et al.

(10) Patent No.: US 9,913,596 B2
(45) Date of Patent: Mar. 13, 2018

(54) SYSTEMS AND METHODS FOR MRI GUIDED TRANS-ORIFICE AND TRANSPERINEAL INTERVENTION APPARATUS WITH ADJUSTABLE BIOPSY NEEDLE INSERTION

(75) Inventors: Axel Krieger, Alexandria, VA (US); Stephen Abellera, Toronto (CA); Iris Elliott, Toronto (CA); Jeremy Bluvol, Toronto (CA); Cameron Piron, Toronto (CA); Chris Luginbuhl, Toronto (CA)

(73) Assignee: INVIVO CORPORATION, Andover, MA (US)

( * ) Notice: Subject to any disclaimer, the term of this patent is extended or adjusted under 35 U.S.C. 154(b) by 1652 days.

(21) Appl. No.: 13/304,573

(22) Filed: Nov. 25, 2011

(65) Prior Publication Data

US 2012/0203095 A1    Aug. 9, 2012

Related U.S. Application Data

(60) Provisional application No. 61/417,271, filed on Nov. 25, 2010, provisional application No. 61/417,270, filed on Nov. 25, 2010.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/6847* (2013.01); *G01R 33/287* (2013.01); *G01R 33/34084* (2013.01); *A61B 8/12* (2013.01); *A61B 2017/00274* (2013.01); *A61B 2017/3411* (2013.01); *A61B 2017/3413* (2013.01); *A61B 2018/00547* (2013.01); *A61B 2090/374* (2016.02); *G01R 33/286* (2013.01)

(58) Field of Classification Search
None
See application file for complete search history.

(56) References Cited

U.S. PATENT DOCUMENTS 4,838,506 A * 6/1989 Cooper ............... A61B 8/4209
                                                          248/200
4,911,173 A * 3/1990 Terwilliger ............. A61B 8/12
                                                          600/101

(Continued)

OTHER PUBLICATIONS

Krieger, "Design and Preliminary Accuracy Studies of an MRI-Guided Transrectal Prostate Intervention System", Med Image Comput Comput Assist Interv. 2007 ; vol. 10: pp. 59-67.*

*Primary Examiner* — Serkan Akar

(57) ABSTRACT

An intervention apparatus is described having a probe with an orifice insertion portion, the insertion portion being configured for insertion into an orifice of a patient. The apparatus also having an intervention tool securement and adjustment mechanism removably attached to the probe. The probe providing support to hold the mechanism in a position relative to the patient, and the adjustment mechanism providing adjustment of an entry point and an angle of entry for an intervention tool to the patient. In embodiments, magnetic resonance imaging, trans-orifice intervention and transperineal intervention are described. Methods for imaging and/or intervention are also described.

16 Claims, 34 Drawing Sheets

(51) Int. Cl.
*G01R 33/34* (2006.01)
*A61B 90/00* (2016.01)
*A61B 18/00* (2006.01)
*A61B 8/12* (2006.01)
*G01R 33/28* (2006.01)
*A61B 17/00* (2006.01)
*A61B 17/34* (2006.01)

(56) References Cited

U.S. PATENT DOCUMENTS

| | | | |
|---|---|---|---|
| 5,871,448 A * | 2/1999 | Ellard | A61B 8/0841 600/459 |
| 2008/0216239 A1* | 9/2008 | Luginbuhl et al. | 5/601 |
| 2010/0036245 A1* | 2/2010 | Yu et al. | 600/439 |
| 2010/0056900 A1* | 3/2010 | Whitcomb | A61B 5/055 600/414 |
| 2011/0218444 A1* | 9/2011 | Steffen | A61B 8/0833 600/461 |

* cited by examiner

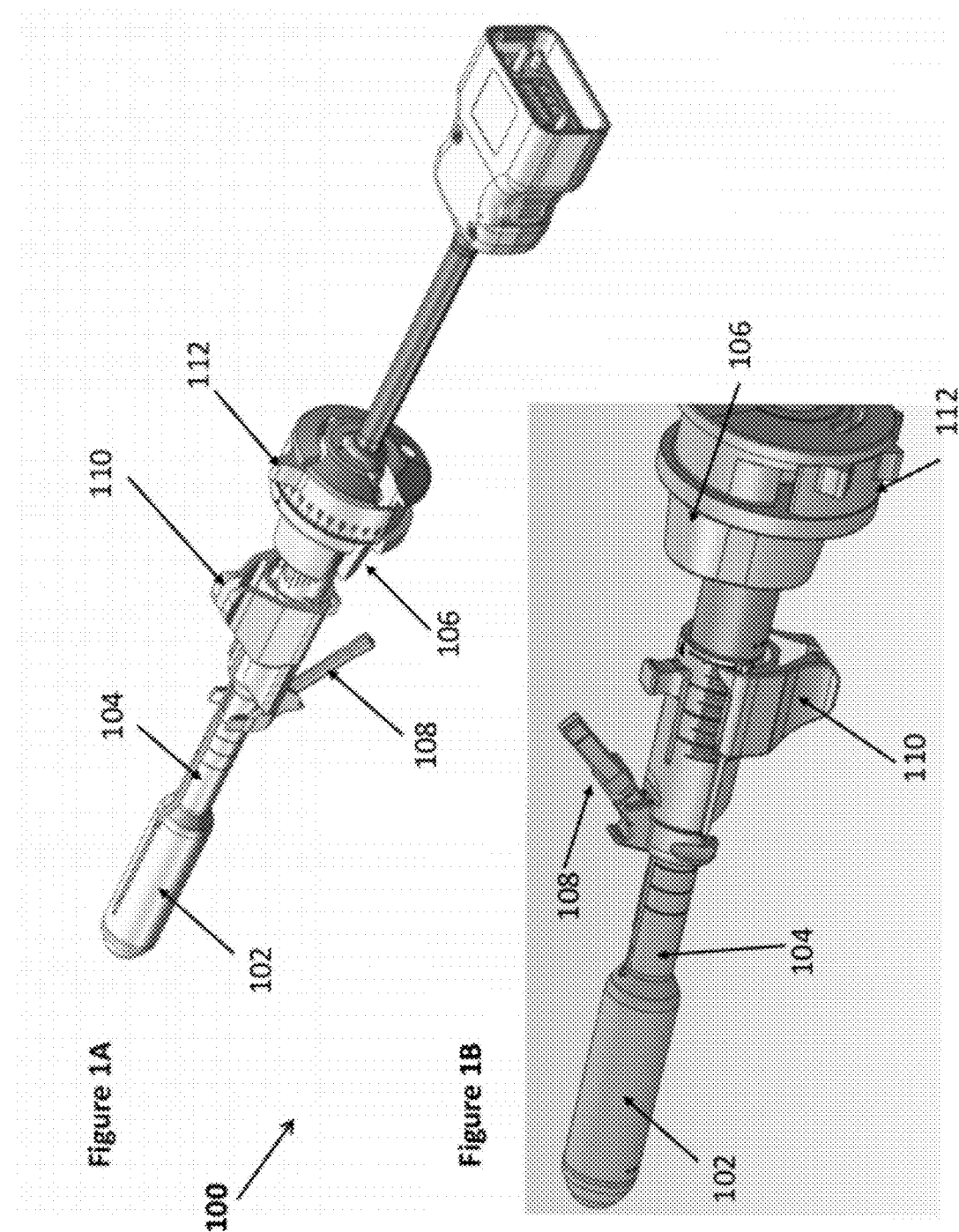

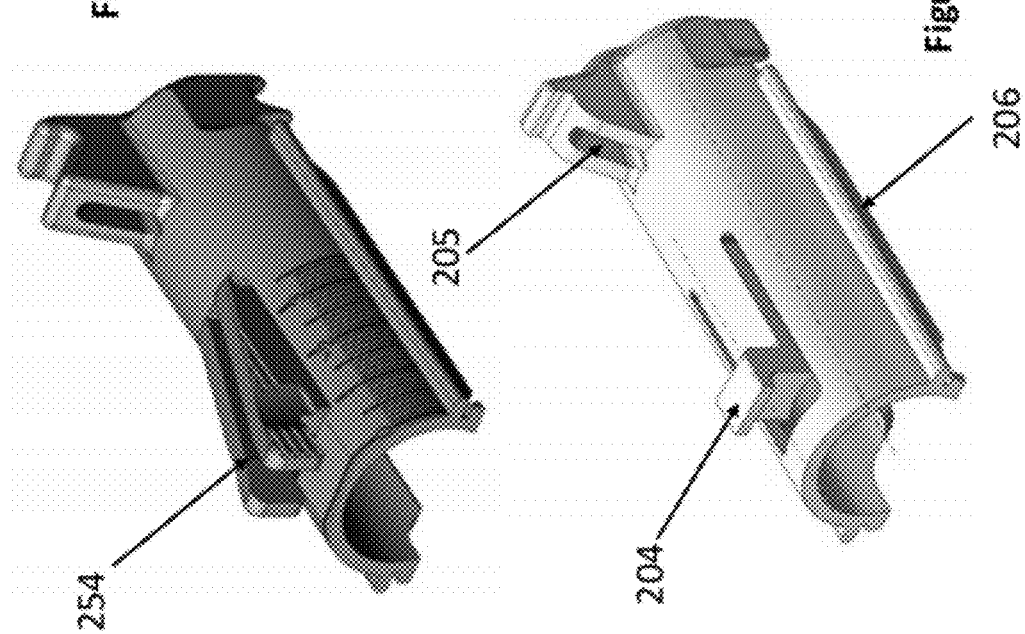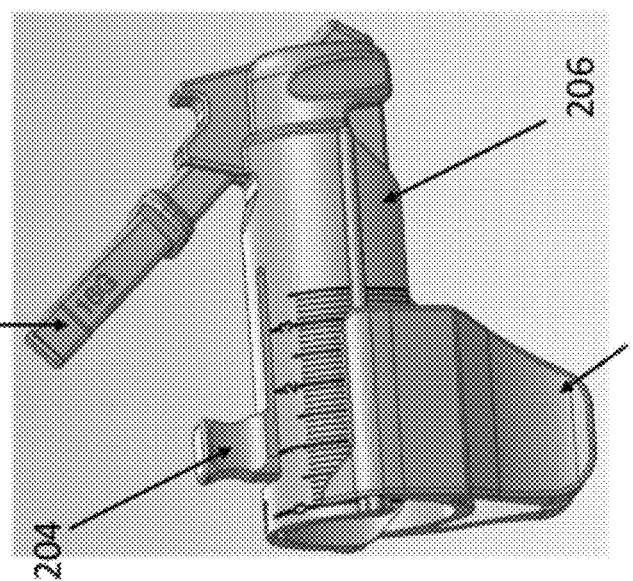

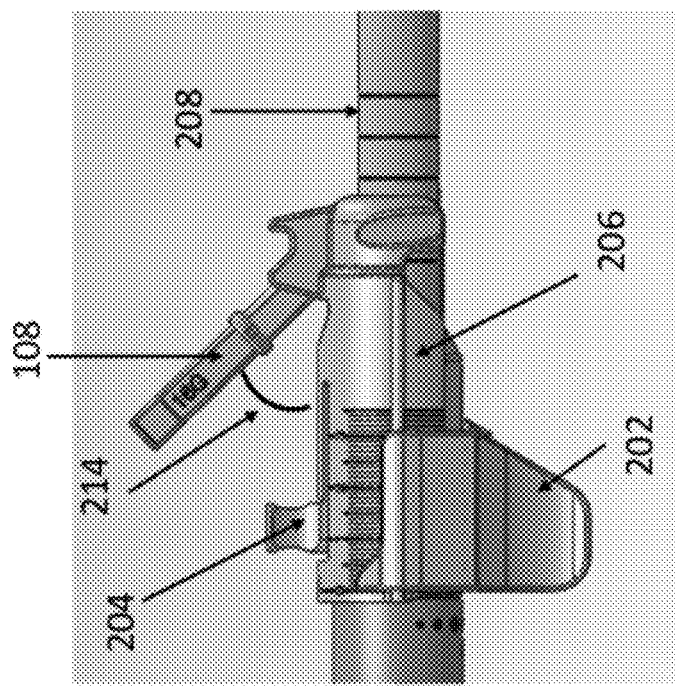

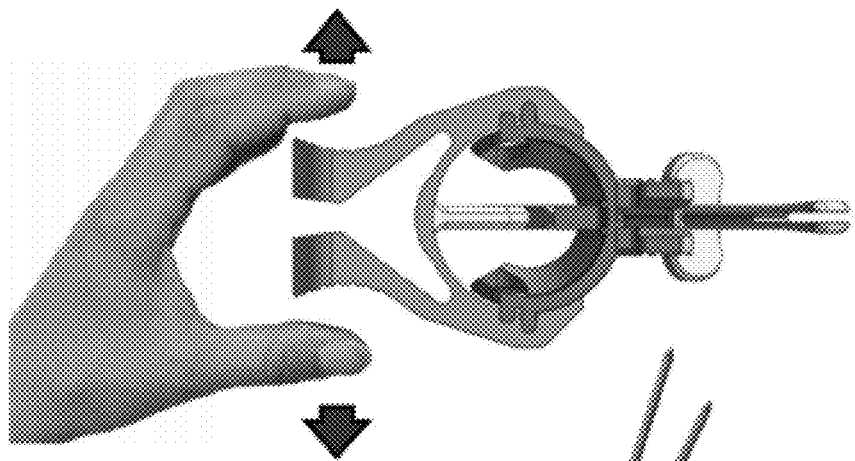
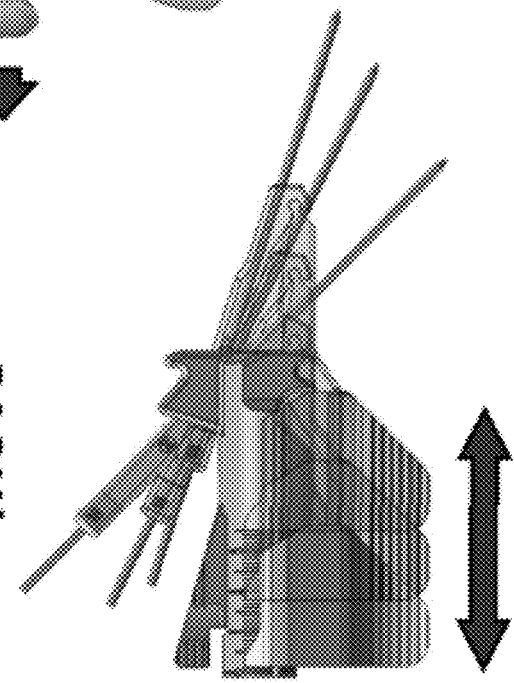
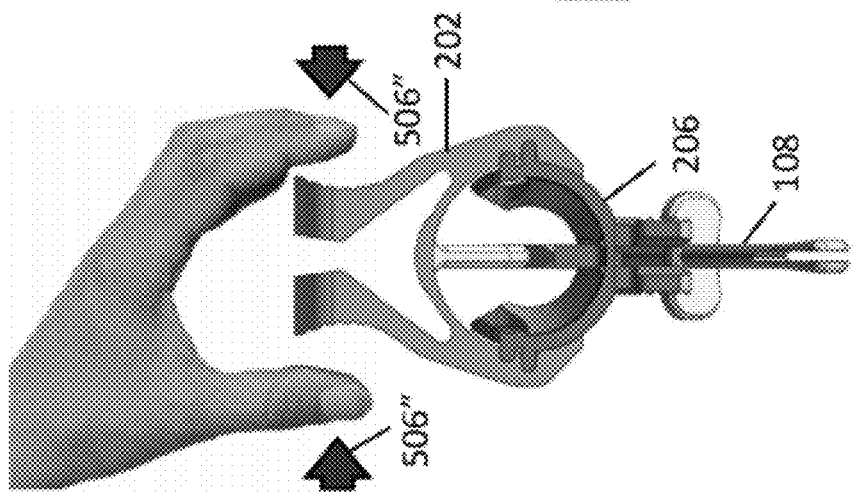
Figure 2E

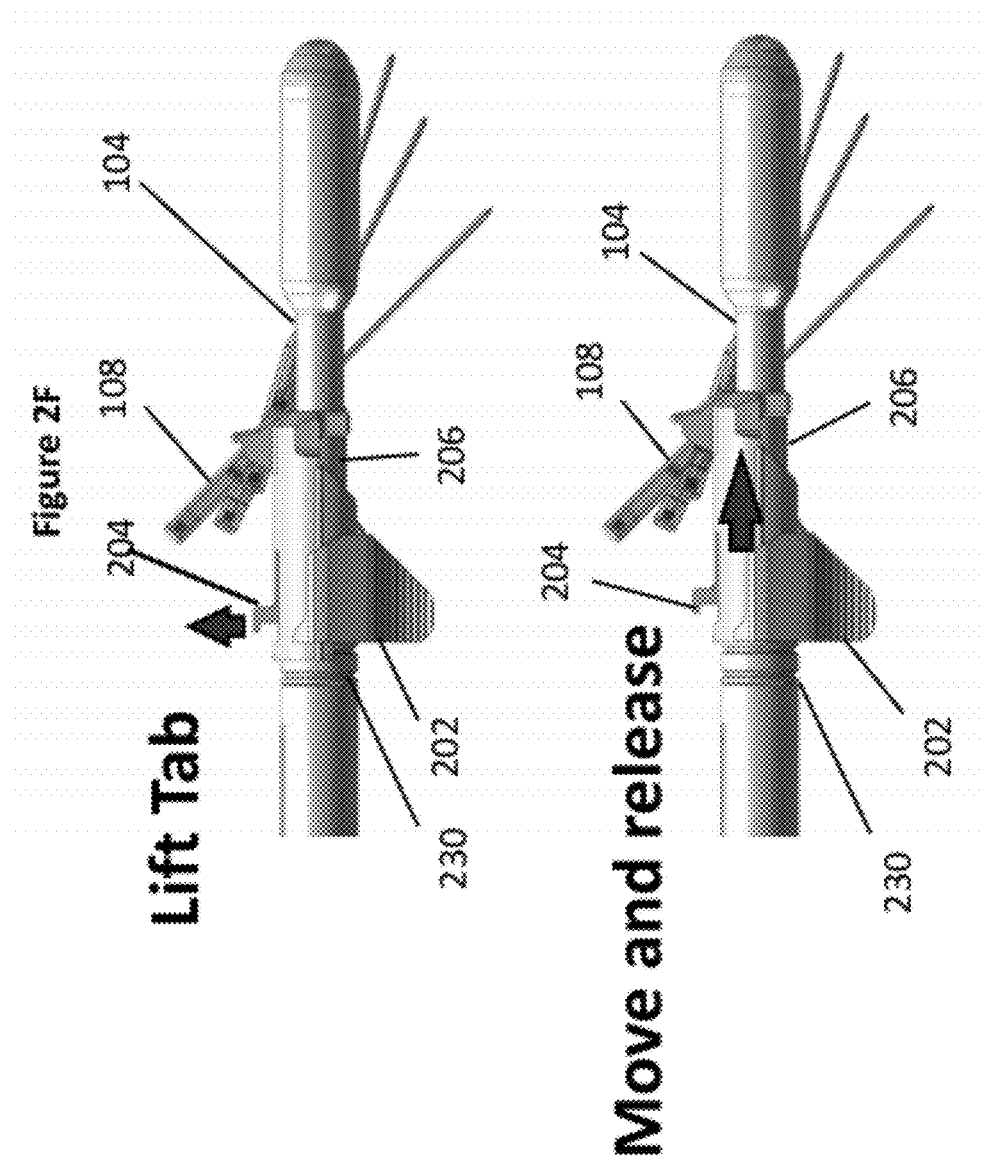

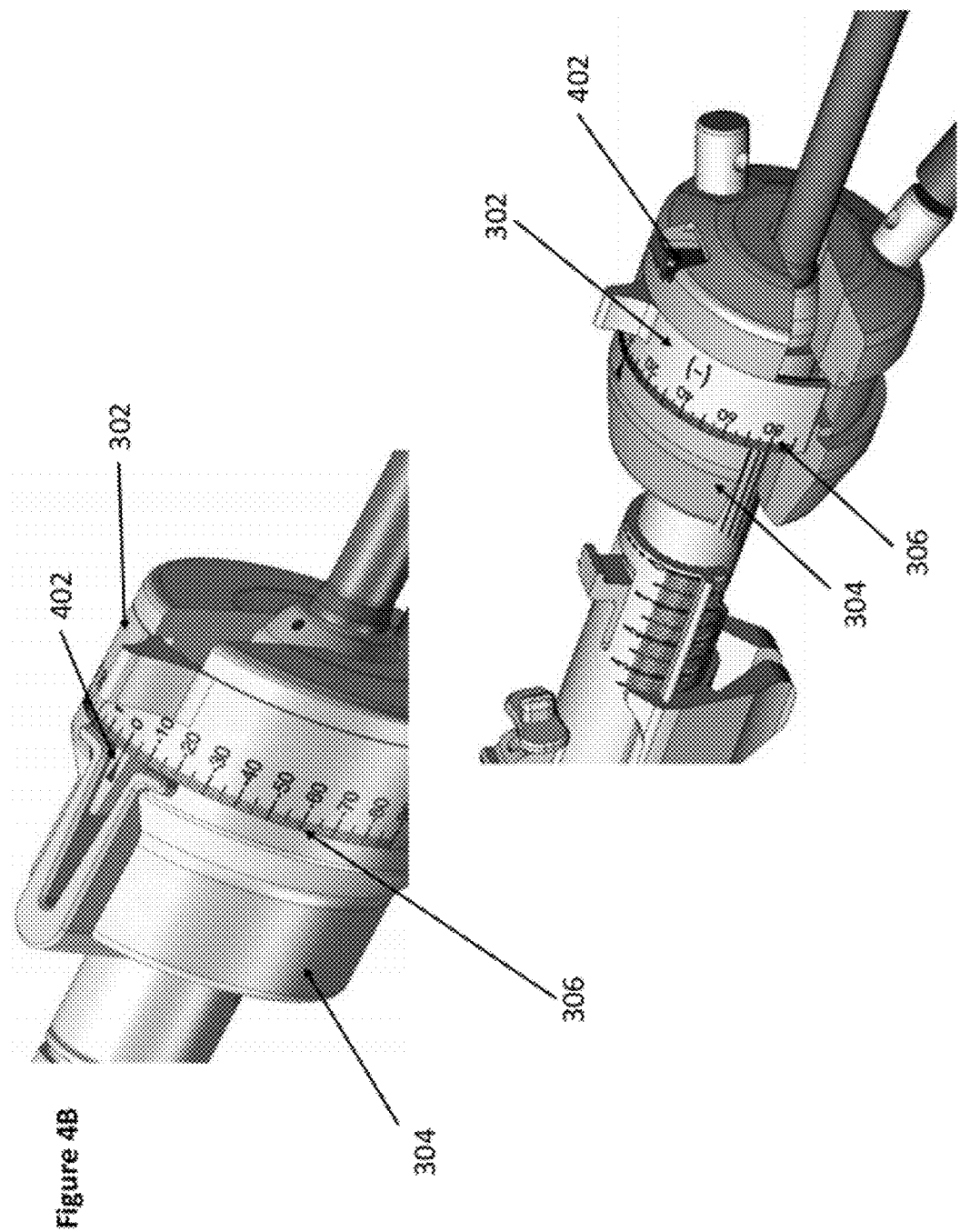

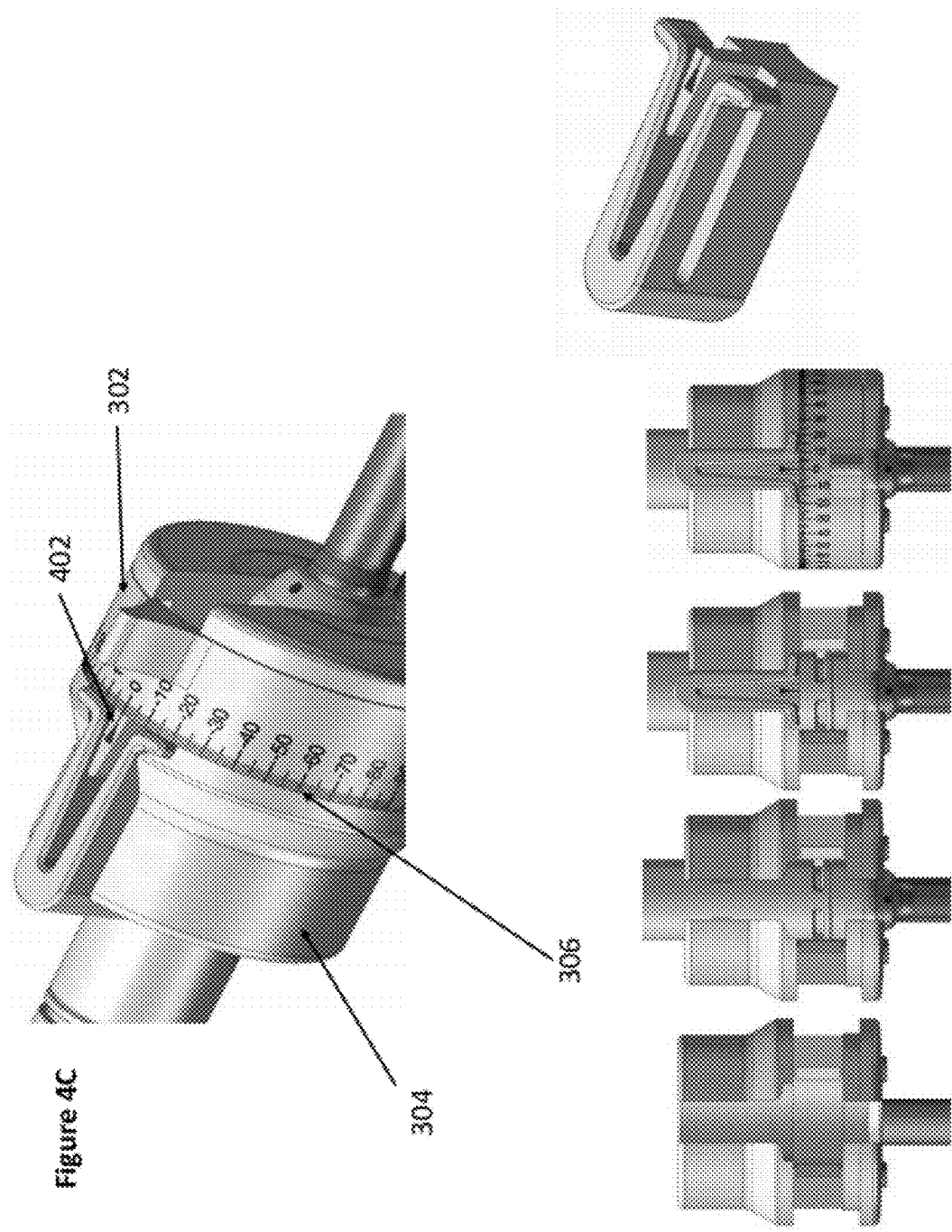

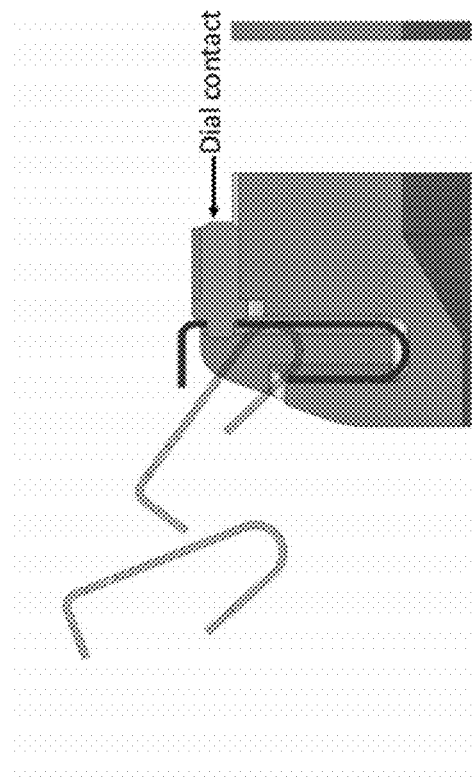
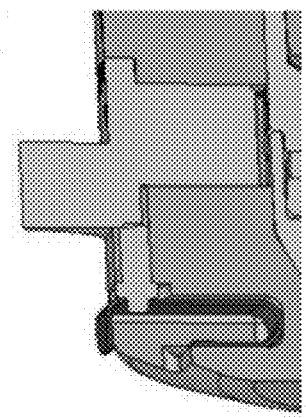
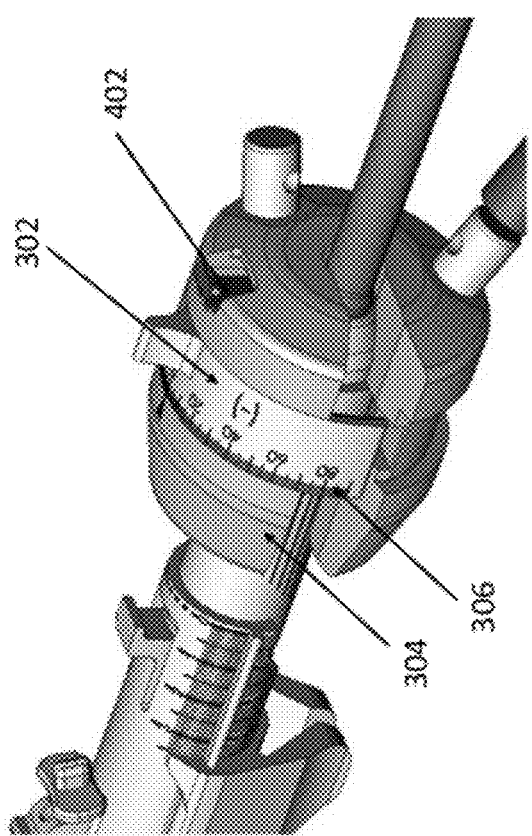
Figure 4D

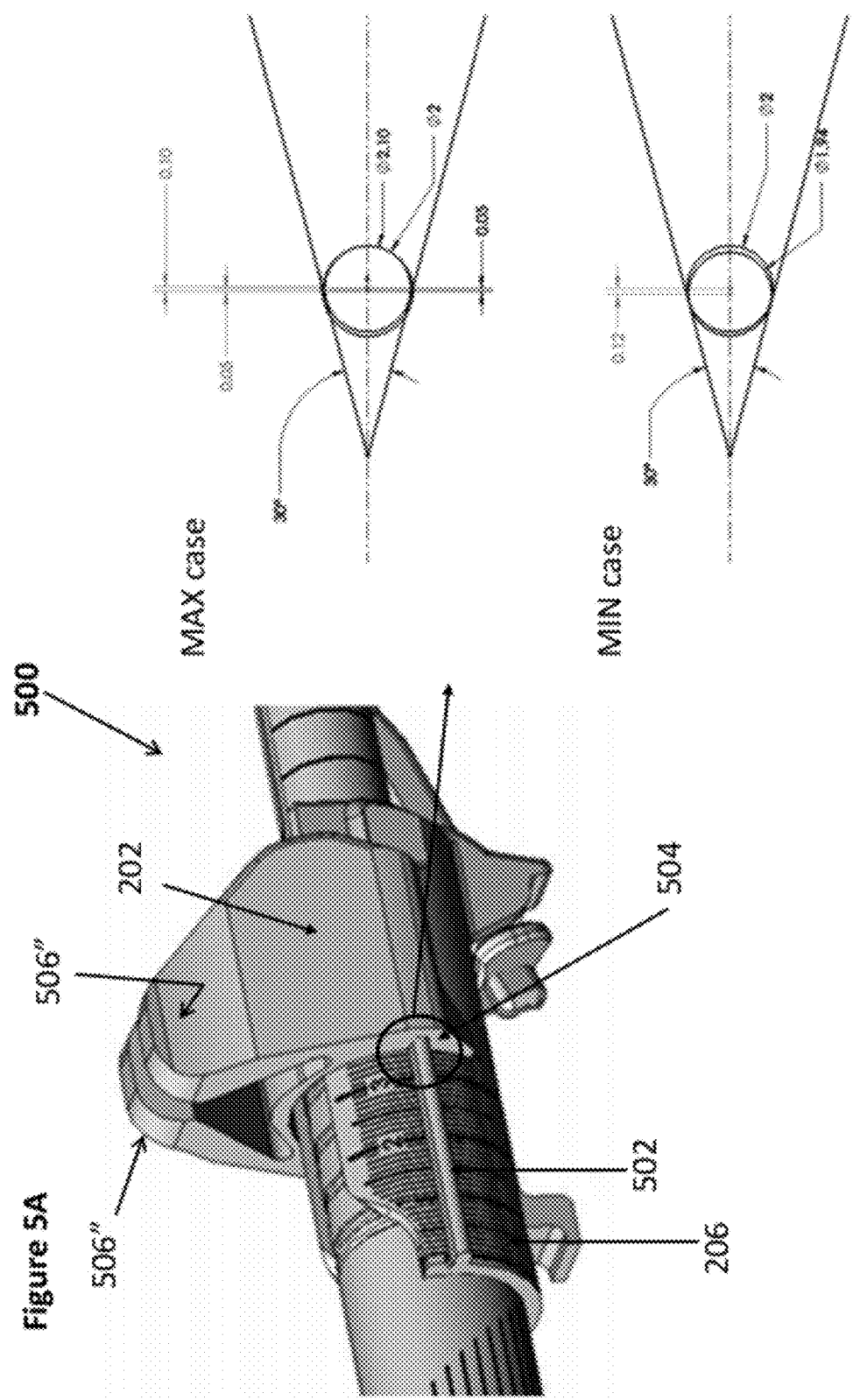

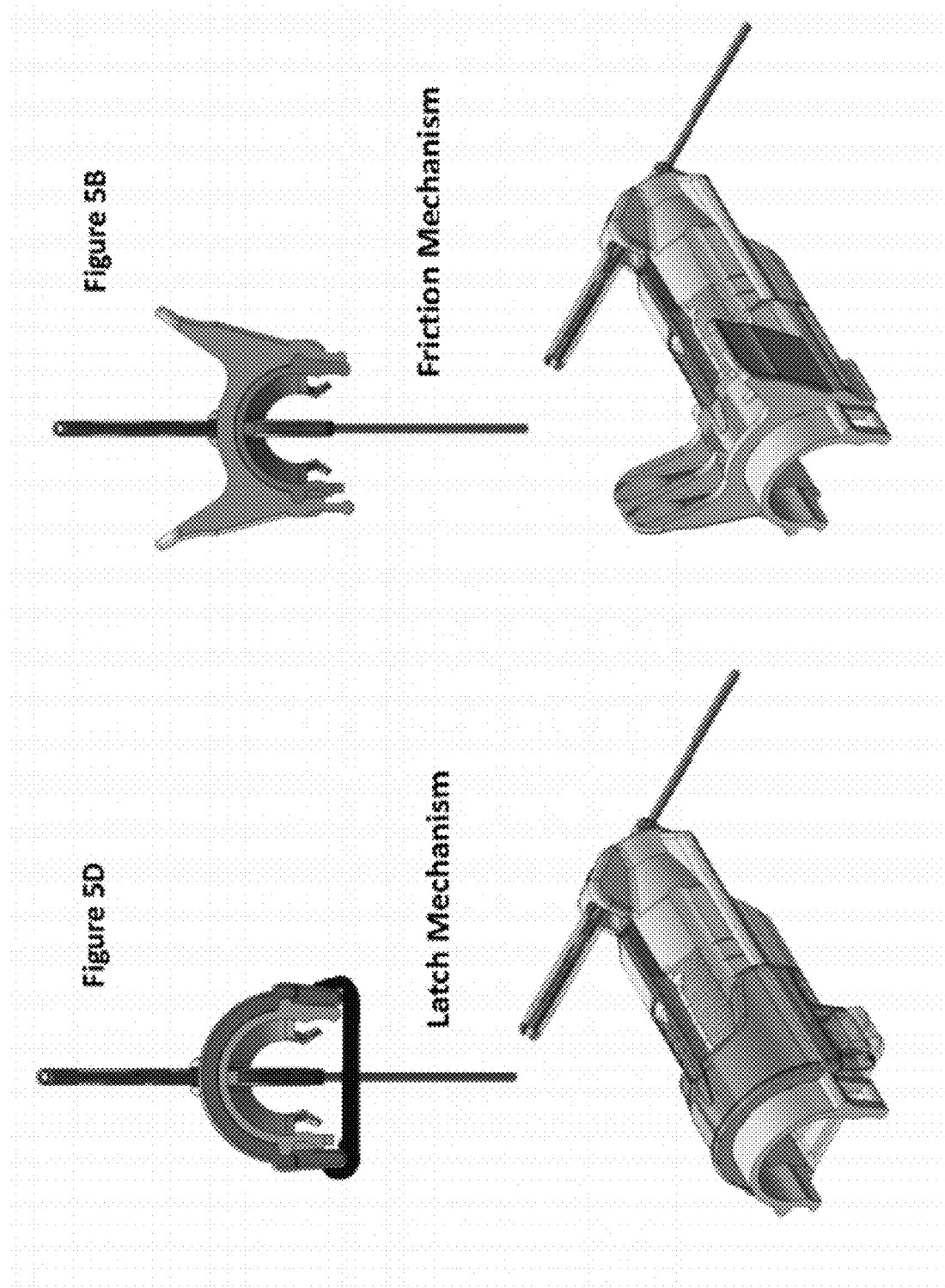

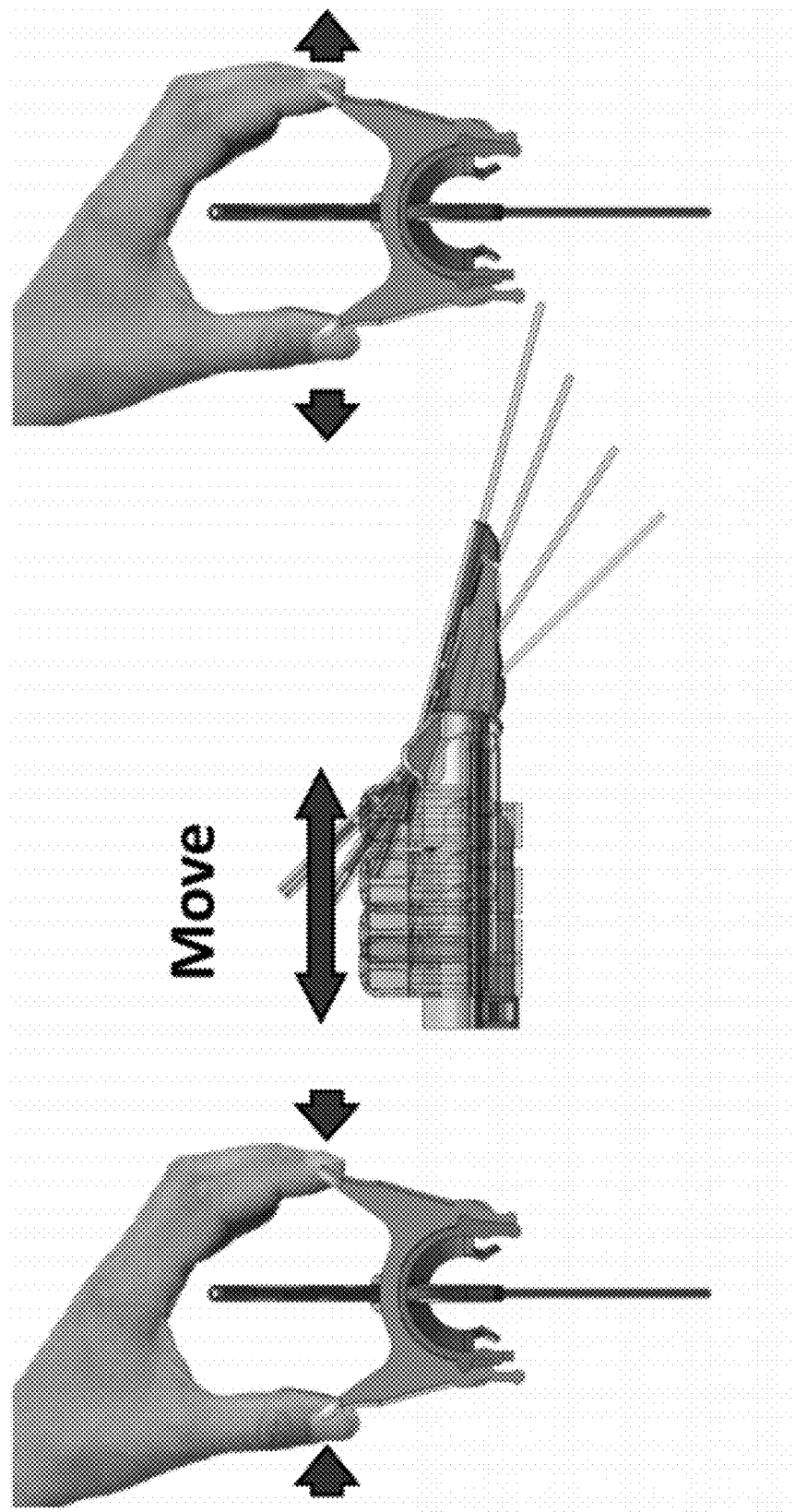

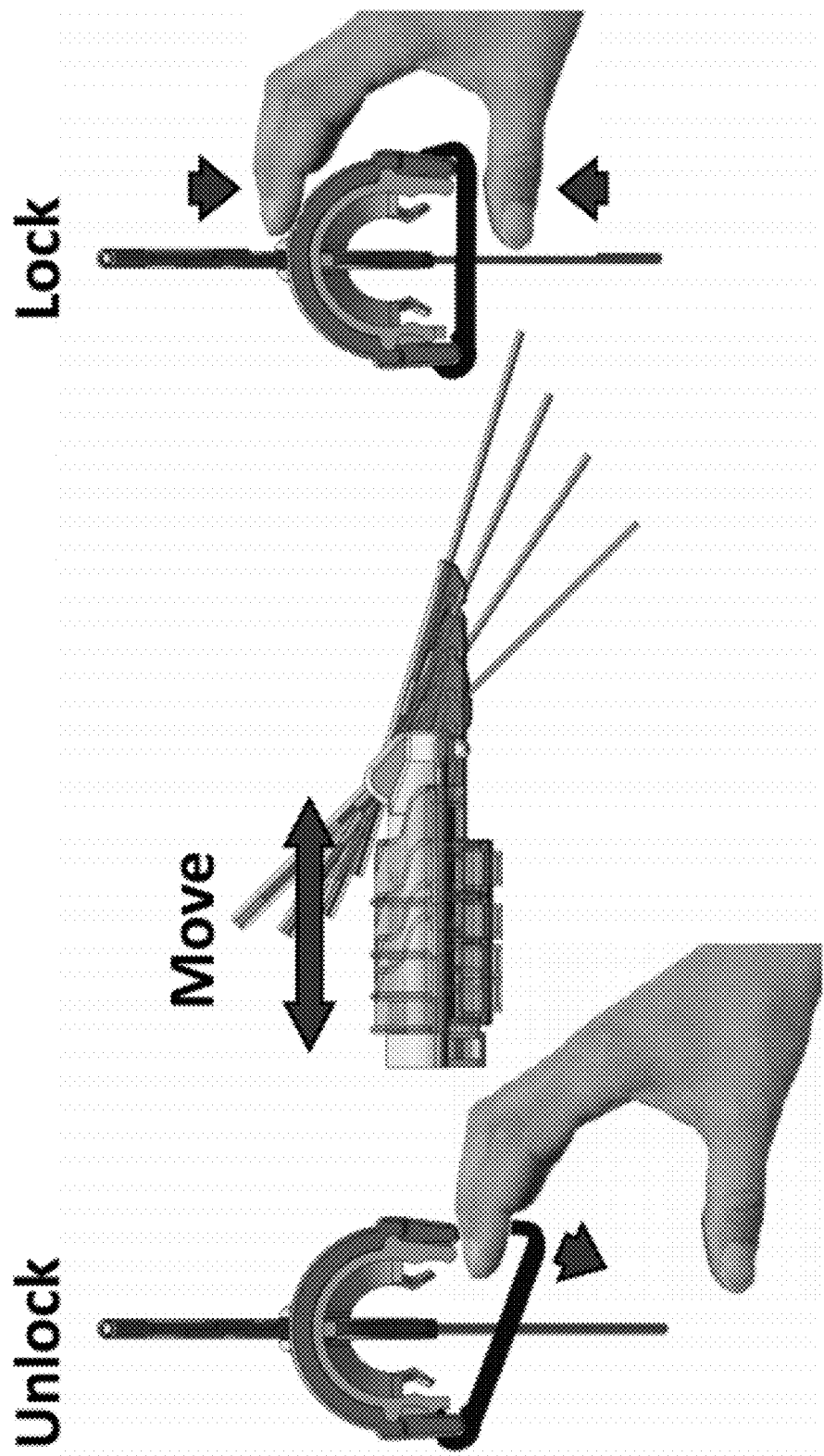

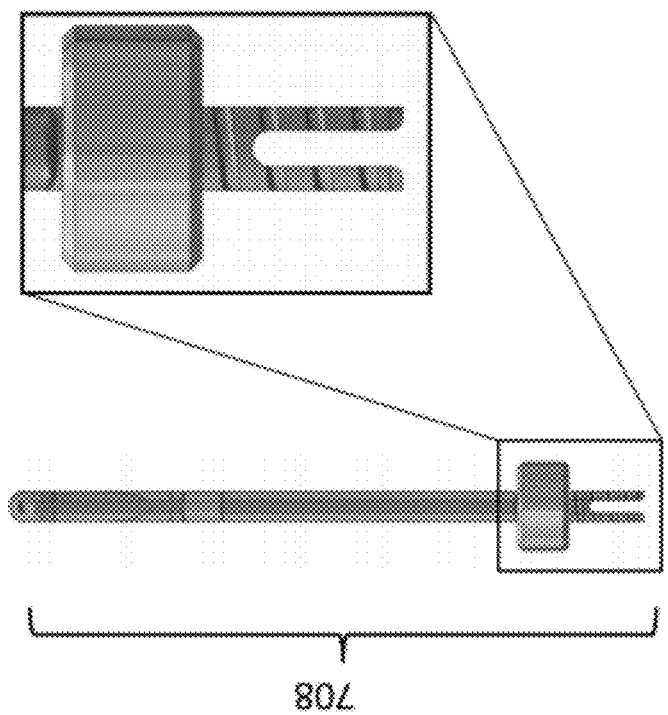
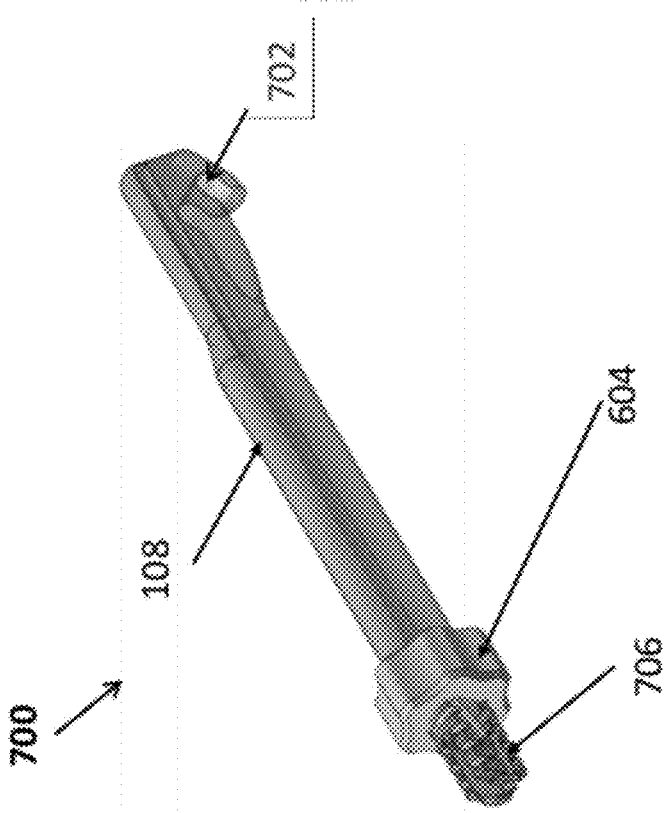

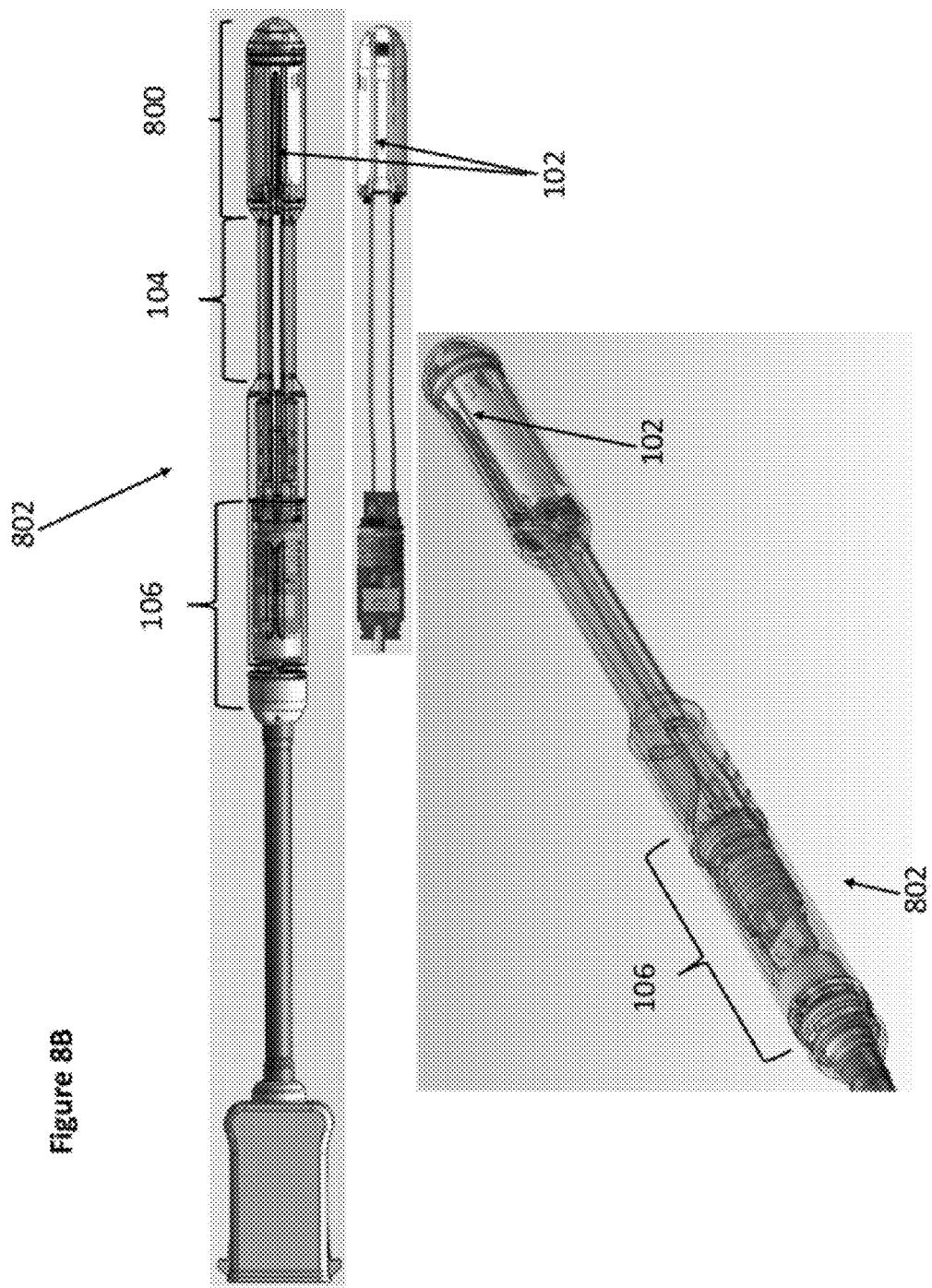

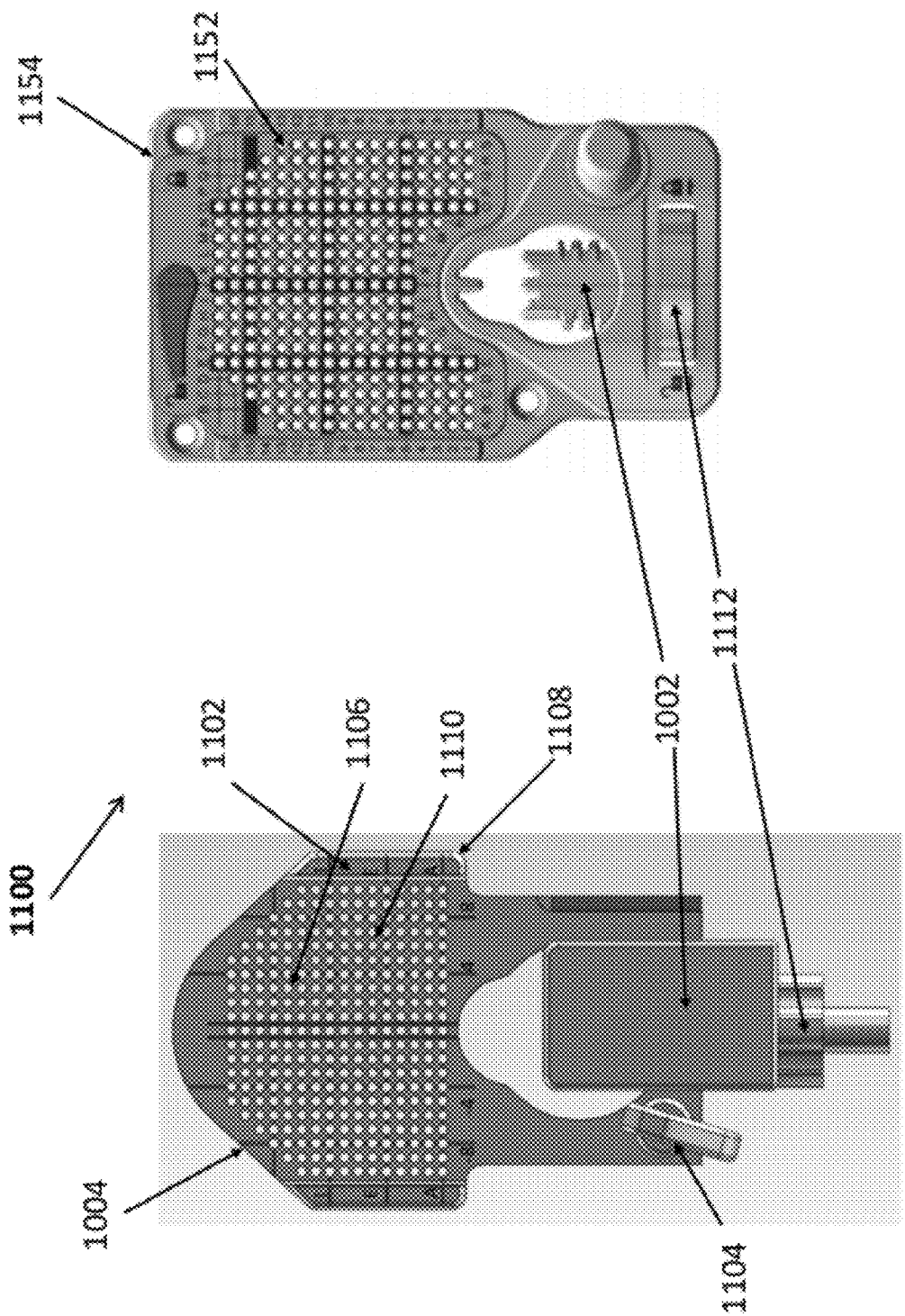

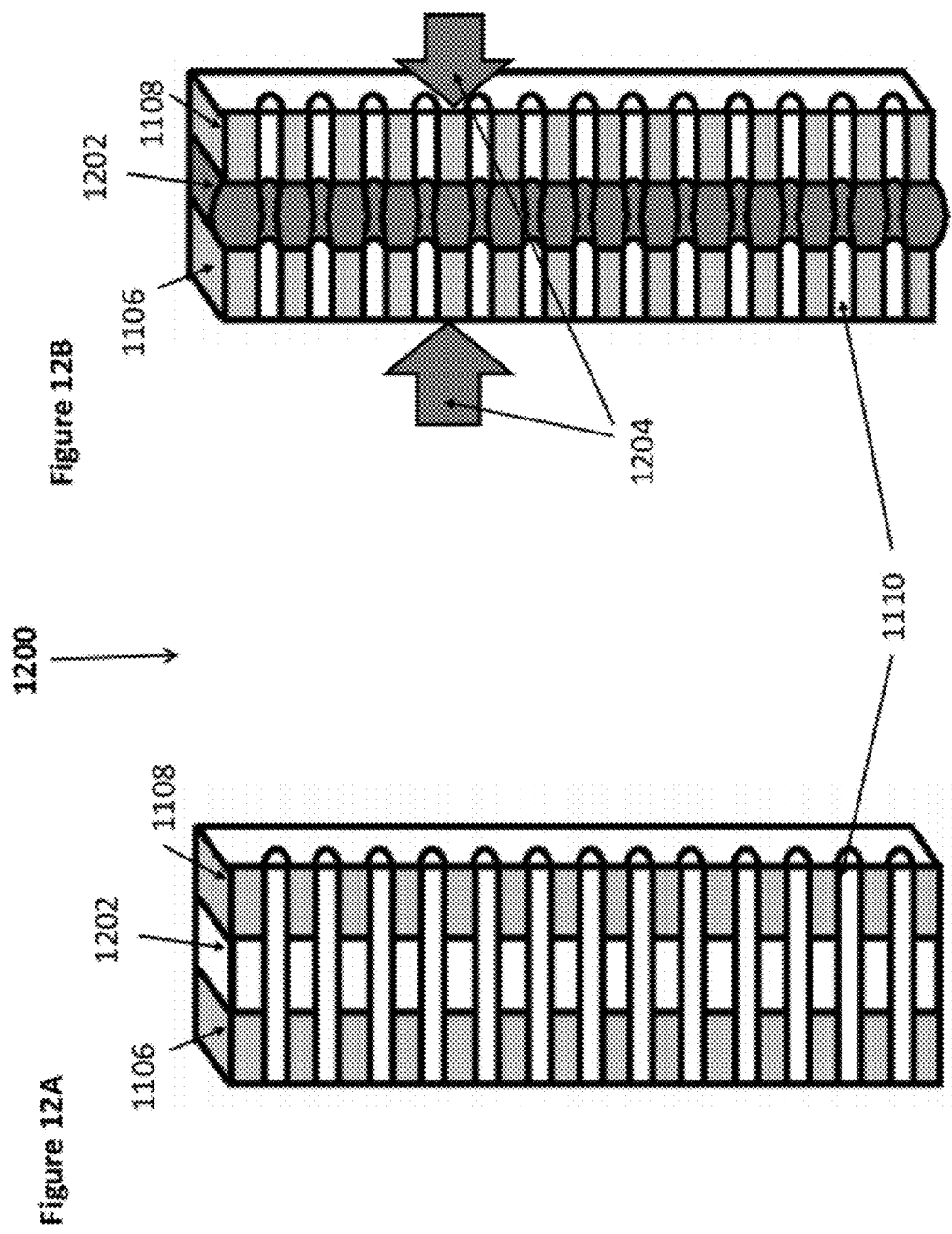

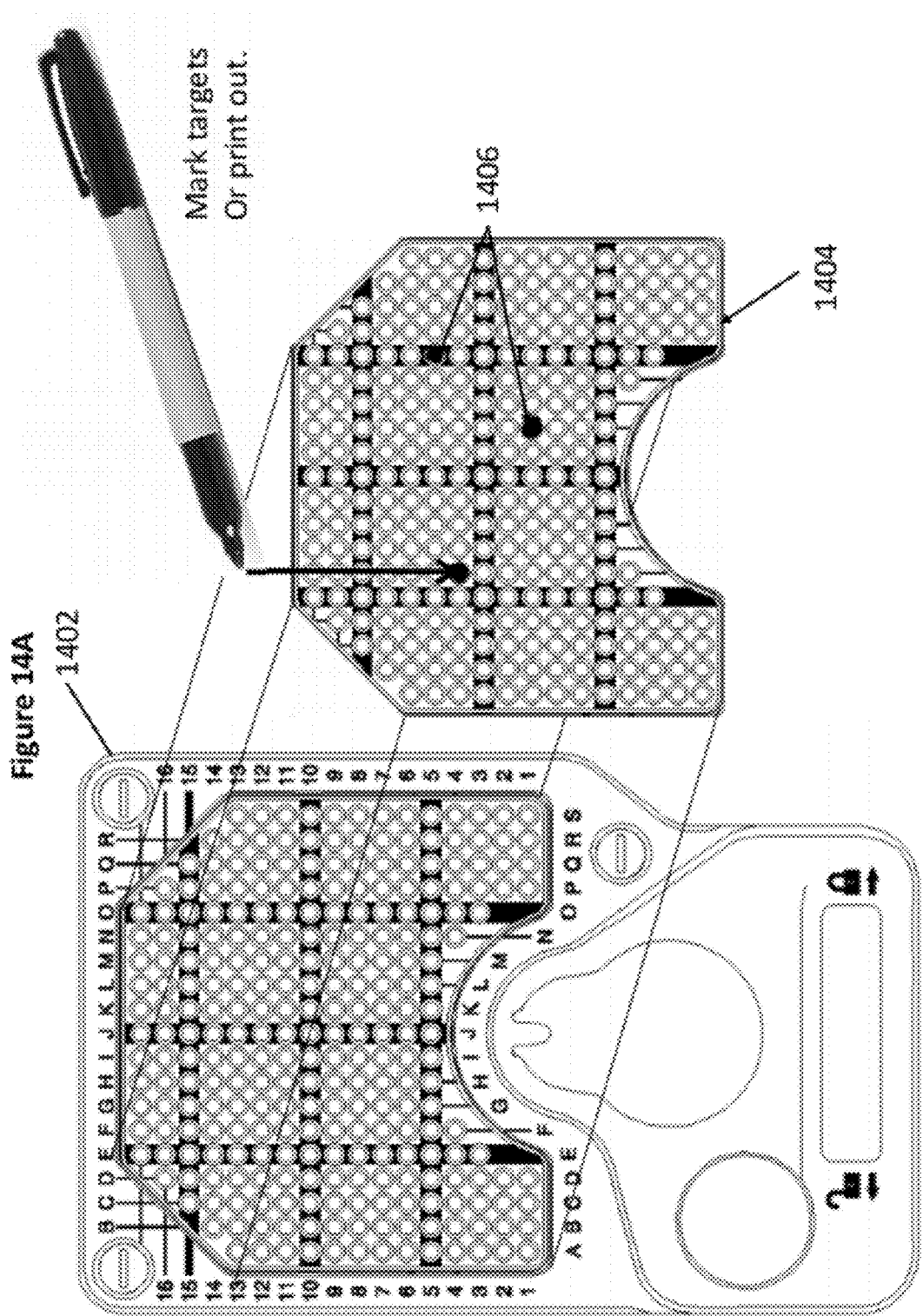

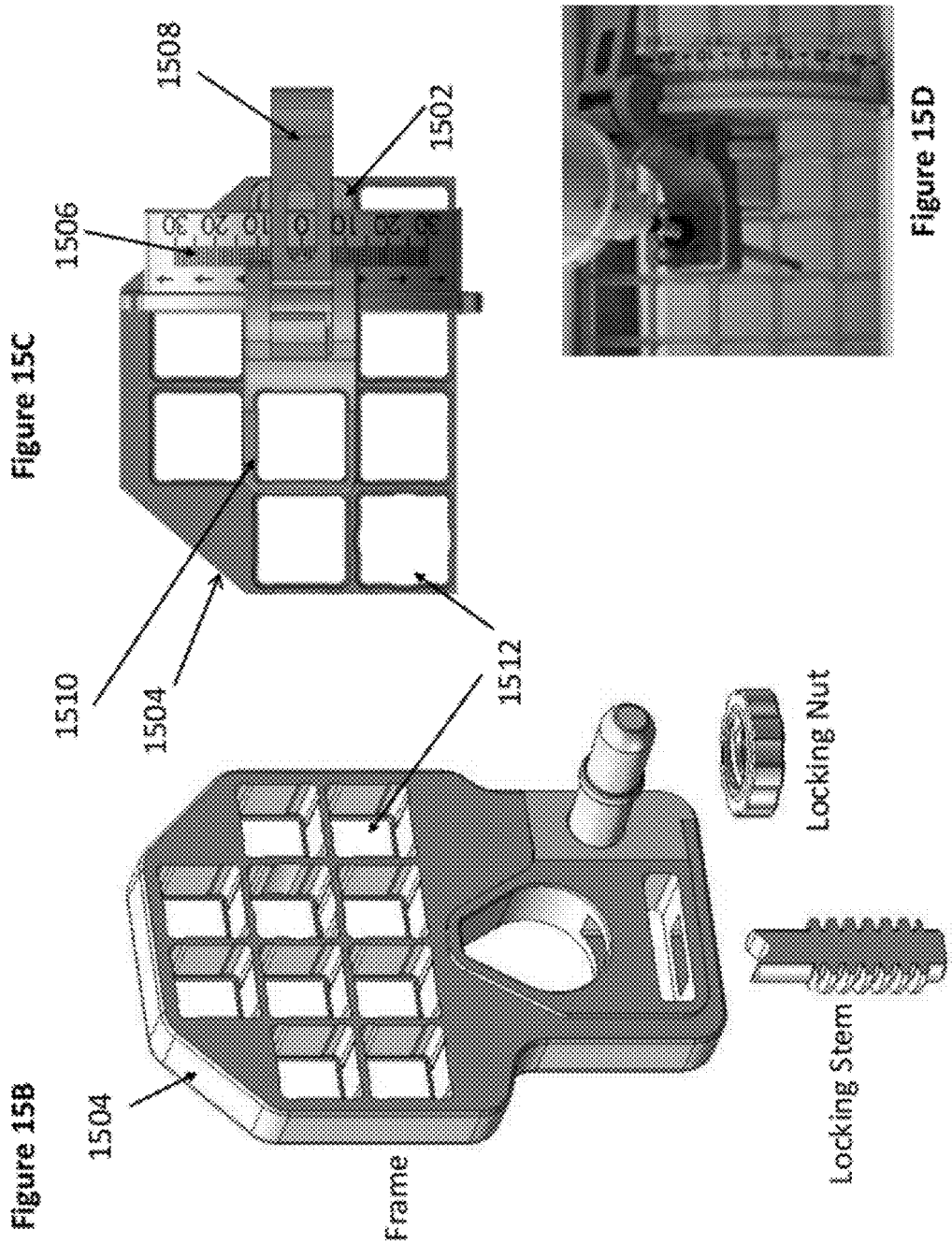

SYSTEMS AND METHODS FOR MRI GUIDED TRANS-ORIFICE AND TRANSPERINEAL INTERVENTION APPARATUS WITH ADJUSTABLE BIOPSY NEEDLE INSERTION

RELATED APPLICATIONS

This application claims priority from U.S. Provisional Application No. 61/417,271 filed Nov. 25, 2010 and U.S. Provisional Application No. 61/417,270 filed Nov. 25, 2010, the contents of each of which are herein incorporated by reference.

FIELD OF INVENTION

This invention relates to a trans-orifice and transperineal guidance and imaging apparatus for directing interventional devices into tissue.

SUMMARY OF THE INVENTION

In an aspect of the invention, there is an intervention apparatus comprising a probe having an orifice insertion portion, the insertion portion being configured for insertion into an orifice of a patient; and an intervention tool securement and adjustment mechanism removably attached to the probe, the probe providing support to hold the mechanism in a position relative to the patient, and the adjustment mechanism providing adjustment of an entry point and an angle of entry for an intervention tool to the patient.

The insertion portion may include an imaging coil, or multiple imaging coils, configured for use with magnetic resonance imaging (MRI) of a tissue of interest in the patient. The MRI of the tissue of interest may provide guidance of the intervention tool to the tissue of interest.

The intervention tool securement and adjustment mechanism may comprise an angle adjustment mechanism operable to adjust the angle of insertion of the interventional tool to the tissue of interest. The angle adjustment mechanism may include a locking mechanism to maintain the angle of insertion of the interventional tool.

The orifice insertion portion of the probe may have a channel therethrough and may have a longitudinal axis. The angle adjustment mechanism may direct the interventional tool through the channel towards the tissue of interest.

The apparatus may further comprise a rotational adjustment mechanism removably attached to the probe and operable to rotate the probe around the longitudinal axis, whereby the angle adjustment mechanism is also rotated around the longitudinal axis.

The intervention tool securement and adjustment mechanism, the rotation adjustment mechanism and the channel of the orifice insertion portion may be configured so that, when the orifice insertion portion of the probe is inserted through the anus of the patient and positioned in the rectum, the intervention tool may be delivered through the channel inter-orifice through the wall of the rectum to the tissue of interest.

The probe may further comprise a neck portion to which the intervention tool securement and adjustment mechanism and the rotation adjustment mechanism may be removably attached. The orifice insertion portion and the neck portion may be substantially cylindrical. The neck portion may have a smaller diameter than the orifice insertion portion. The intervention tool securement and adjustment mechanism may include an intervention tool locking mechanism thereon, to secure the intervention tool in a desired position.

The intervention tool securement and adjustment mechanism may be configured so that, when the orifice insertion portion of the probe is inserted through the anus of the patient, the intervention tool may be delivered transperineally to the tissue of interest.

The intervention tool securement and adjustment mechanism may further comprise a second imaging coil, or multiple coils, configured for use with MRI of the tissue of interest in the patient.

The intervention tool locking mechanism may comprise a hole passing through a first plate, a second plate and an elastomer plate between the first and second plates, for accepting the intervention tool therethrough; a compressing mechanism configured to act on the first and second plates to compress the elastomer plate, whereby upon compression of the elastomer plate, the elastomer expands at least in a direction perpendicular to the compression, decreasing the diameter of the hole at the elastomer plate to secure the intervention tool passing therethrough. The angle adjustment mechanism may be removably attached to the intervention tool securement and adjustment mechanism.

In another aspect of the present invention, there is a method for imaging and performing intervention on a tissue of interest in a patient, comprising: inserting a magnetic resonance imaging (MRI) coil housed within a probe through the anus of the patient; obtaining MRI information associated with the tissue of interest through the MRI coil; and using the MRI information, guiding an intervention tool to the tissue of interest through an intervention tool securement and adjustment mechanism removably attached to the probe. The intervention tool may pass through the portion of the probe inserted through the anus of the patient, whereby the intervention tool passes through the wall of the rectum towards the tissue of interest.

The intervention tool may pass transperineally into the patient towards the tissue of interest. The intervention tool securement and adjustment mechanism may further comprise a second MRI coil, which can tend to increase the quality of the images of the region of interest that can be obtained, and/or provide additional associated with the tissue of interest, for use in guiding the intervention tool to the tissue of interest, or diagnosis.

BRIEF DESCRIPTION OF DRAWINGS

For a better understanding of embodiments of the system and methods described herein, and to show more clearly how they may be carried into effect, reference will be made by way of example, to the accompanying drawings in which:

FIGS. 1A and 1B show isometric views of an embodiment of an intervention tool securement and adjustment mechanism;

FIGS. 2A to 2G show embodiments of an angle adjustment mechanism for the guidance system;

FIGS. 4A to 4D show isometric views of an embodiment of a rotation locking mechanism of the rotational adjustment mechanism shown in FIGS. 3A and 3B;

FIG. 5A shows an isometric view of an embodiment of an angle locking mechanism for the angle adjustment mechanism shown in FIGS. 2A-2E;

FIGS. 5B to 5E show alternate locking mechanisms for angle adjustment;

FIG. 7A shows an isometric view of an alternate embodiment of a needle lock screw for the angle adjustment mechanism shown in FIGS. 2A-2E;

FIG. 7B shows a side view of the needle lock screw shown in FIG. 7A;

FIG. 8B shows subsurface views of the trans-orifice guidance apparatus shown in FIG. 8A;

FIGS. 11A and 11B show views of embodiments of a needle locking system;

FIGS. 12A and 12B show isometric views of an embodiment of a needle locking system;

FIG. 14A shows a label system to identify specific needle holes in an intervention tool securement and adjustment mechanism;

FIG. 15B shows an isometric view of a frame to adjust needle angles in the intervention tool securement and adjustment mechanism shown in FIG. 15A;

FIGS. 15C and 15D show views of an angle plug to adjust needle angles in the intervention tool securement and adjustment mechanism shown in FIGS. 15A and 15B.

DETAILED DESCRIPTION

Figure 2A:
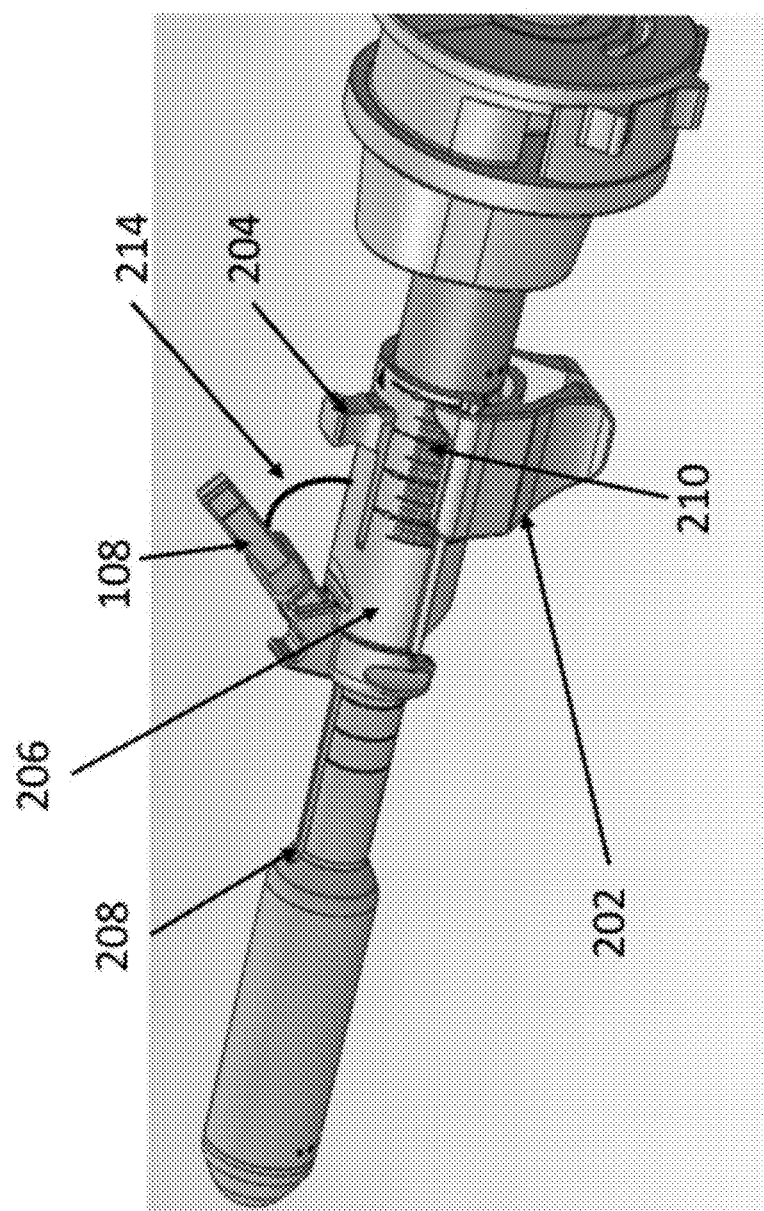

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

Prostate, cervical and colorectal diseases represent significant health problems in the United States; metastatic prostate cancer is the third leading cause of death among American men over fifty years, and currently resulting in approximately 31,000 deaths annually.

One type of diagnostic and/or intervention method for these types of cancer is through the use of interventional devices capable of obtaining core needle biopsies. Additionally, the treatment of prostate, cervical, colorectal and related disease may be provided by way of interventional devices providing such therapies as cryotherapy, laser therapy, irreversible electroporation, radiofrequency ablation, radiation market placement and high and low dose brachytherapy.

In addition, imaging systems such as Magnetic Resonance Imaging (MRI), sonographs (ultrasound), fluoroscopy, X-ray, and the like can provide visual guidance when locating an interventional device, such as a biopsy needle, in relation to treatment or therapy-targeted tissue. These modalities can generate imaging data that can be used to determine the appropriate positioning of the interventional device or instrument.

A common diagnostic method for prostate, cervical and colorectal cancers includes using MRI imaging which has a high sensitivity for detecting tumors. However, current MRI systems do not allow MRI imaging and interventions, such as biopsies, to be performed concurrently. Without concurrent intervention with MRI imaging, diagnostic specificity can be significantly reduced. For example, biopsies taken based on previously recorded images may result in poorer sampling of target tissue, as the time delay may have resulted in changes in tumor dimension and placement within the body.

The diagnostic sensitivity of some high field MRI scanners can also be limited, in part by the size and shape of such devices. For example, whole-body magnets that surround the patient completely do not allow access to the patient during imaging as the workspace inside the bore of the whole-body magnet is limited. Consequently, conventional medical robotics, or mechanical linkages, do not fit inside the whole-body magnet, preventing concurrent biopsies and other intrusive activities from being performed at the time of imaging.

MRI imaging techniques in prostate, cervical and colorectal biopsies and related localized therapies, are also limited by the strength of the magnetic field being generated within the whole-body magnet, which can be about 200,000 times stronger than the magnetic field of the earth. Due to these strong magnetic fields, ferromagnetic materials and electronic devices must remain outside of the magnetic field for safety and/or imaging concerns. Traditional electro-mechanical robots and mechanical linkages may not be useable within the MRI bore during scanning, preventing contemporaneous access to patients for biopsy purposes.

While open, rather than closed bored MRIs may facilitate patient access, open MRI are limited in disease diagnosis as they tend to have weaker magnetic fields than those generated by closed magnets. A characteristic of this weaker magnetic field is that open magnets tend to have lower signal-to-noise ratio, than that exhibited by closed magnets, and thus resulting in lower imaging quality. While these lower quality images may be acceptable when used in certain environments, such as in research environments or for producing high quality images of anatomy that is close to the skin surface, these magnets are generally seen as deficient in more critical applications, such as the diagnosis of prostate cancer.

As a result, current MRI techniques, in both open and closed bores, may not provide a means of effectively imaging tissue of interest, while contemporaneously allowing for the biopsy of affected tissue.

In addition to MRI, another commonly used technique in the diagnosis of prostate cancer, is transrectal ultrasound (TRUS) guided needle biopsy. TRUS guidance is also the primary technique for contemporary intraprostatic delivery of therapeutics. Under this technique, needles are placed into tissue, typically the prostate, manually while observing some intra-operative guiding images generated by real-time transrectal ultrasound. This technique has been overwhelmingly popular due to its excellent specificity, real-time nature, low cost, and apparent simplicity. At the same time, however, TRUS-guided biopsy can tend to fail to correctly detect the presence of prostate cancer in some cases.

One of the primary limitations of the TRUS guided needle biopsy is that TRUS biopsy is executed entirely by free hand. TRUS, which typically uses transrectal needle placement, can be controlled by generating transrectal ultrasound and template jigs; however, it is still dependent on the physician or operator's hand-eye coordination. Therefore, the outcomes of TRUS guided procedures show significant variability among practitioners. In medical or health procedures, use of some guides can improve the accuracy of instrument placement into tissue.

In addition to the issues of free-hand biopsies and contemporaneous biopsy and imaging, current methods of prostate cancer diagnosis typically apply transperineal needle placement for both biopsy and brachytherapy. With this placement, the needle is inserted through the skin between the scrotum and the rectum, and into the prostate. While this may be a conventionally accepted method for therapy, it tends to be an invasive route, as the needle must pass through a number of tissues before reaching the prostate. Therefore it may be desirable to have a system to perform biopsies or other procedures through a minimally intrusive path or trajectory, such as through the wall of an existing orifice of the patient, such as the rectum.

With reference to FIGS. 1A and 1B, an embodiment of an intervention tool securement and adjustment mechanism is shown, as attached to a probe that, in the embodiment, operates in trans-orifice guidance apparatus 100 for use in interventional procedures, such as biopsies. In the embodiment of FIGS. 1A and 1B, guidance apparatus 100 comprises head section 102, neck 104, handle section 106 and angle adjustment mechanism 110. Angle adjustment mechanism 110 includes needle tube 108 (however skilled persons will appreciate that in some embodiments needle tube 108 may be a separate element capable of removable engagement to angle adjustment mechanism 110). Apparatus 100 also includes rotation adjustment mechanism 112.

In some embodiments, head section 102 may be an orifice insertion section, for insertion into an orifice of a patient. In such embodiments, head section 102 may include imaging apparatus, such as MRI coils for imaging a tissue of interest in a patient when trans-orifice intervention guidance apparatus 100 is in use. For example, head, or coil, section 102 as shown can be inserted into a patient's rectum through the anus and can be positioned proximate to the patient's prostate. The patient can then be positioned in an MRI magnet to obtain images of the patient's prostate for intervention and/or analysis.

Coil section 102 is connected to handle section 106 by neck 104. In the embodiment shown, neck 104 has a smaller diameter than coil section 102, which can provide additional patient comfort when coil section 102 is inserted entirely within a patient's rectum, the patient's anus closing around the smaller diameter neck 104, which can be more comfortable for the patient and can tend to provide additional securement of trans-orifice intervention guidance apparatus 100 when in use.

In some embodiments, coil section 102 can have alternative shapes to account for differently sized coils for different body cavity insertion points and variations in patent anatomy. In other embodiments, coil section 102 can be comprised of composite tubing to allow coil section 102 to exhibit generally non-rigid properties, capable of conforming to the shape of various organs, imaging needs and/or tissues past the points of body cavity insertion.

With additional reference to FIGS. 2A-E an embodiment of angle adjustment mechanism 110 is shown comprising adjustment slider 202, tab 204, saddle 206, needle tube 108, track (or slot) 208 and angle scale 210. In the embodiment shown, angle adjustment mechanisms 110 adjusts angle 214 to a desired angle, to allow an interventional device inserted through needle tube 108 to reach a desired anatomical part of a patient when the head, or coil, section 102 and, in some embodiments, a portion of neck 104, have been inserted into an orifice or existing body cavity of the patient.

In the embodiment shown in FIG. 2A-E, track 208 also tends to prohibit over-extension of an intervention device held by needle tube 108, and tends to ensure that needle tube 108 travels along a straight path.

In the embodiment shown, when trans-orifice guidance apparatus 100 is in use, medical instruments, such as biopsy needles, can be inserted through needle tube 108. In some embodiments, medical instruments can additionally include lasers, electroporators, catheters, or other medical instruments capable of taking biopsies of or delivering treatments to tissue in a patient. Such treatments can include cryotherapy, laser therapy, irreversible electroporation, radiofrequency ablation, radiation marker placement and high and low dose brachytherapy treatment. In some embodiments, needle tube 108 can include a reusable or sterilizable insert which can be removed and cleaned for further uses.

In some embodiments, lifting tab 204 on saddle 206, allows saddle 206 to be linearly displaced along the length of trans-orifice guidance apparatus 100 (such as along neck section 108). In some embodiments the path along which saddle 206 can be repositioned may be limited by stopping means such as projections or changes in diameter of trans-orifice guidance apparatus 100 (shown as grooves 230 in the embodiment of FIG. 2F, which can interact with tab 204 to hold saddle 206 into place). An alternate release mechanism 254 to tab 206 usable in other embodiments is shown in FIG. 2G, with release achieved by pinching the wings of mechanism 254.

In the embodiments shown, angle adjustment mechanism 110 can be displaced in discrete positions along angle scale 210 by slider 202. Angle adjustment mechanism 110 mechanically engages needle tube 108 by saddle 206 and slider 202. In the embodiment, needle tube 108 is generally only moving along its longitudinal length through bore 205 of saddle 206, while it is also engaged to slider 202, such that movement of slider 202 along saddle 206, such as over scale 210, causes angle 214 of needle tube 108 to change as needle tube 108 is moved with slider 202 relative to saddle 206, as shown in FIG. 2E.

Reference is now made to FIG. 5A, which shows an embodiment of angle locking mechanism 500 having saddle rails 502 on saddle 206, and slider clips 504 on slider 202 for engaging rails 502. In use, as illustrated in FIG. 2E, when pressure is applied to the slider 202 along the direction 506" as shown, this tends to flex the slider body and lift slider clips 504 off saddle 206 and saddle rails 502, allowing the slider 202 to be linearly displaced in along scale 210. In the embodiment shown, this linear displacement results in an angular displacement of needle tube 108 (as discussed above). In the embodiment shown, when pressure on slider 202 along 506" is released, slider clips 504 will then re-engage saddle rails 502 with sufficient force to hold, or lock, slider 202 and needle tube 108 into place to prevent unwanted movement. Skilled persons will appreciate that other means can be used to lock and unlock the slider 202 and/or needle tube 108, to allow and prevent unwanted linear and/or angle displacement.

In some embodiments, components of angle locking mechanism 500 can be snapped on to handle portion of the probe in one direction and held into place. This removable configuration tends to make the angle locking mechanism 500, which houses the interventional device, disposable for sanitary purposes.

An alternative embodiment of frictional engagement mechanism for engaging with rails 502 on saddle 206, in which the slider has wings that are further spaced apart, is shown in FIGS. 5B and 5C. A still further embodiment of an engagement mechanism that uses a latch to secure a slider in place relative to a saddle's rails is shown in FIGS. 5D and 5E.

In some embodiments, angle 214 of needle tube 108 is adjustable between a predefined minimum and predefined maximum. In such embodiments, when needle tube 108 is set at the predefined minimum, this can allow a medical instrument, such as a biopsy needle, to interact with proximal tissue (relative to coil section 102) of the patient, and when set at the predefined maximum can allow for interaction with distal tissue (relative to coil section 102) of the patient. In the embodiment shown if FIG. 2D, a range of motion of slider 202, such as 4 cm, can translate needle tube 108 along the angular range of 17 to 45 degrees for angle adjustment 110, while rotation adjustment 112 can provide +/−90 degrees of rotation (or 180 degrees total).

In other embodiments, a user can modify angle 214 by manually adjusting needle tube 108, which may, or may not be connected to a slider 202. In such embodiments, needle tube 108 can be connected to rotate between multiple degrees of freedom, if desired, for example, if needle tube 108 is connected to a gimble joint. Skilled persons will appreciate that other means may be used to adjust angle 214 of needle tube 108 and to hold the desired angle.

Figure 6B:
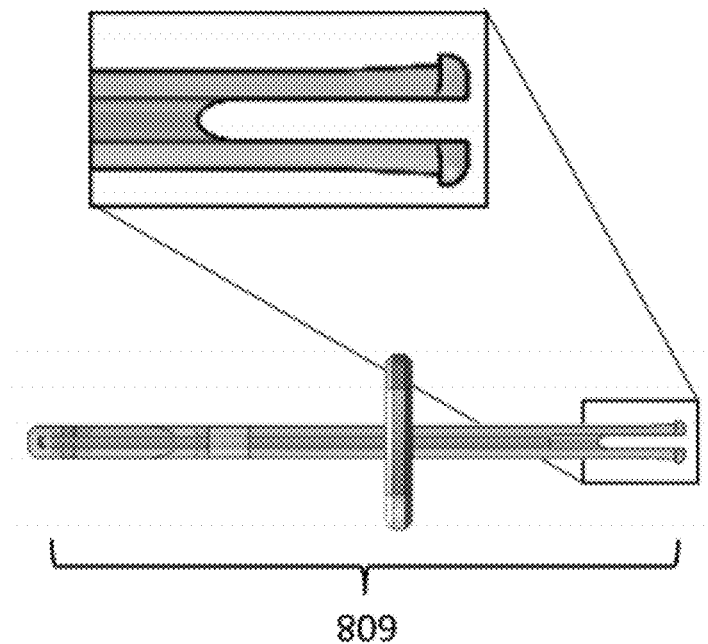
FIG. 6B shows a side view of the needle lock slide shown in FIG. 6A.
Figure 6A:
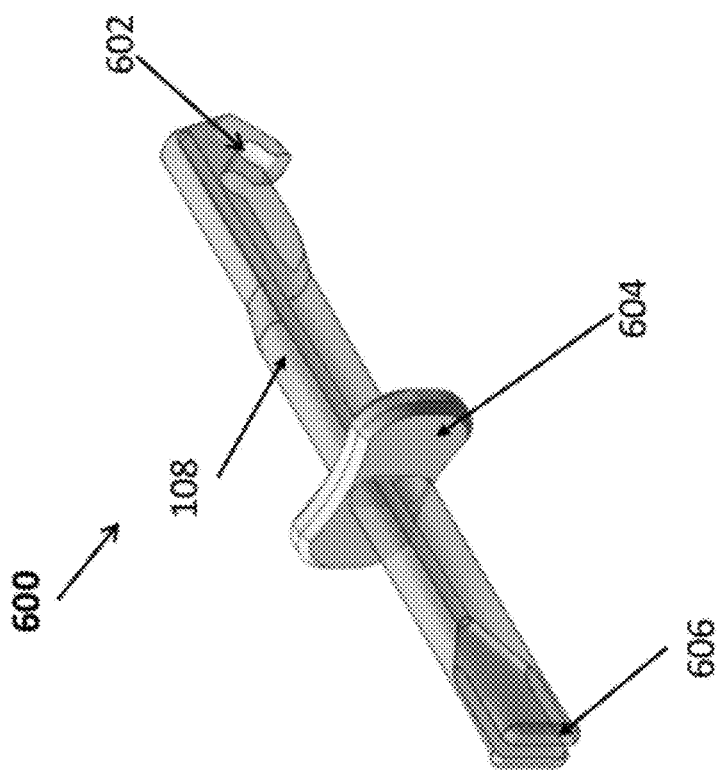
FIG. 6A shows an isometric view of an embodiment of a needle lock slide for the angle adjustment mechanism shown in FIGS. 2A-2E.

With further reference to FIGS. 6A and 6B an embodiment of a needle lock slide mechanism 600 for use as needle tube 108, is shown. As shown, mechanism 600 comprises needle tube 608, joint 602 for engaging with slider 202, cinching plate 604 and wings 606. Needle lock slide mechanism 600 provides a locking means to restrict unwanted movement of needle tube 608 and any medical instrument therein, such as a biopsy needle, or alternate interventional device, after the linear position of slider 202 has been positioned and/or adjusted. In the embodiment shown, a medical instrument, such as a biopsy needle, or other interventional device is placed between wings 606 and through the tube. When pressure is applied to wings 606, such as by cinching plate 604 being slid over them, wings 606 collapse inward, which can constrict the space between wings 606, and can lock a medical instrument between wings 606, such as a biopsy needle, or interventional device into position restricting unwanted movement.

Referring now to FIGS. 7A and 7B, an alternative locking mechanism for needle tube 108 is shown, as needle lock screw mechanism 700. Mechanism 700 comprises needle tube 708, joint 702 for engaging slider 202, nut 704 and wings 706. Needle lock screw mechanism 700 can be used to lock the position of a medical instrument, such as a biopsy needle, or other interventional device in a desired position within needle tube 708. A medical instrument, such as a biopsy needle, or other interventional device can be positioned between wings 706 and through the tube, and when nut 704 is screwed over wings 706, wings 706 will tend to collapse inward so as to constrict the space between the wings 706, and tending to lock an instrument, such as a biopsy needle, into the position it has been currently positioned in and prevent unwanted movement of such instrument.

Figure 3A:
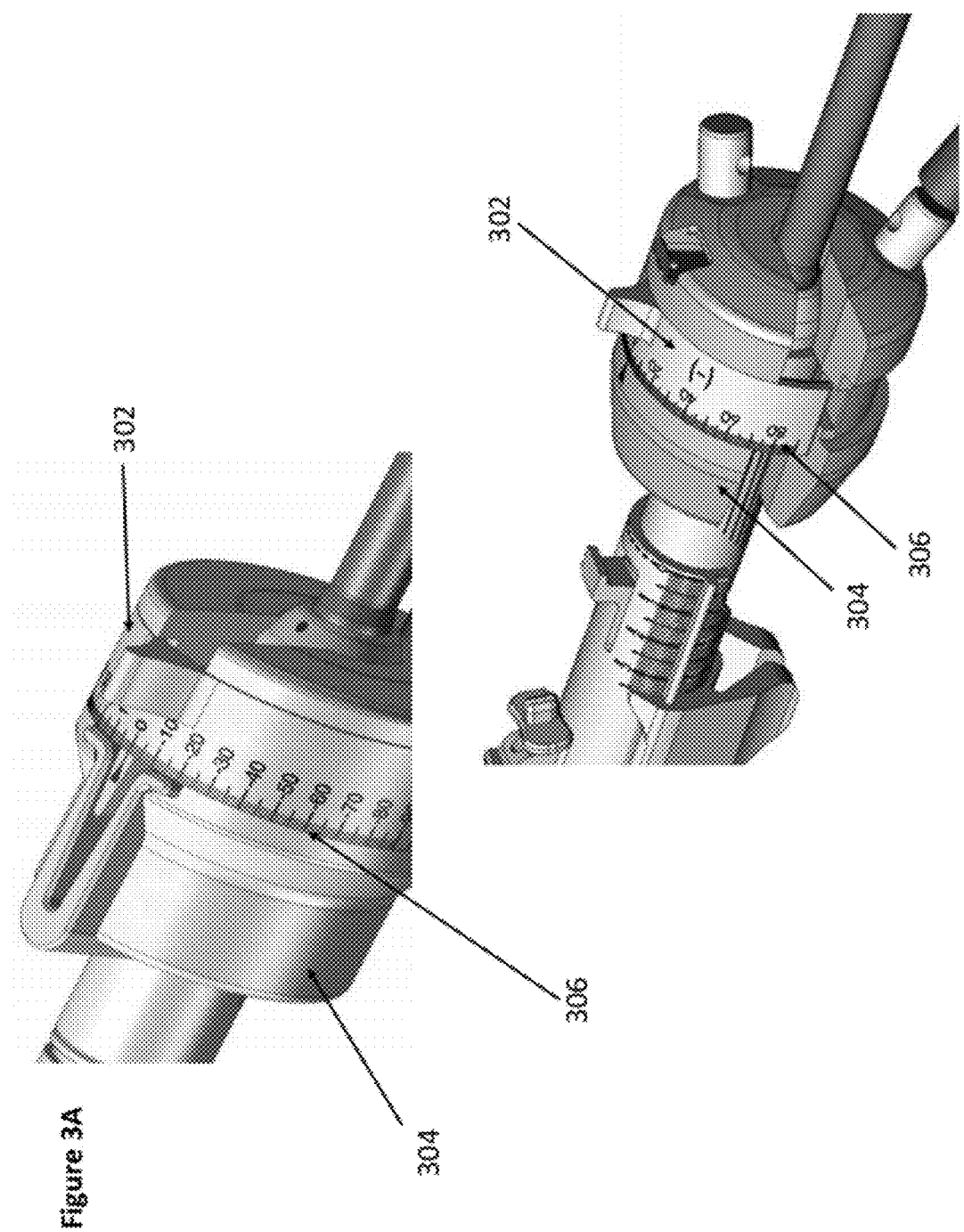
FIG. 3A shows isometric views of a rotational adjustment mechanism.
Figure 3B:
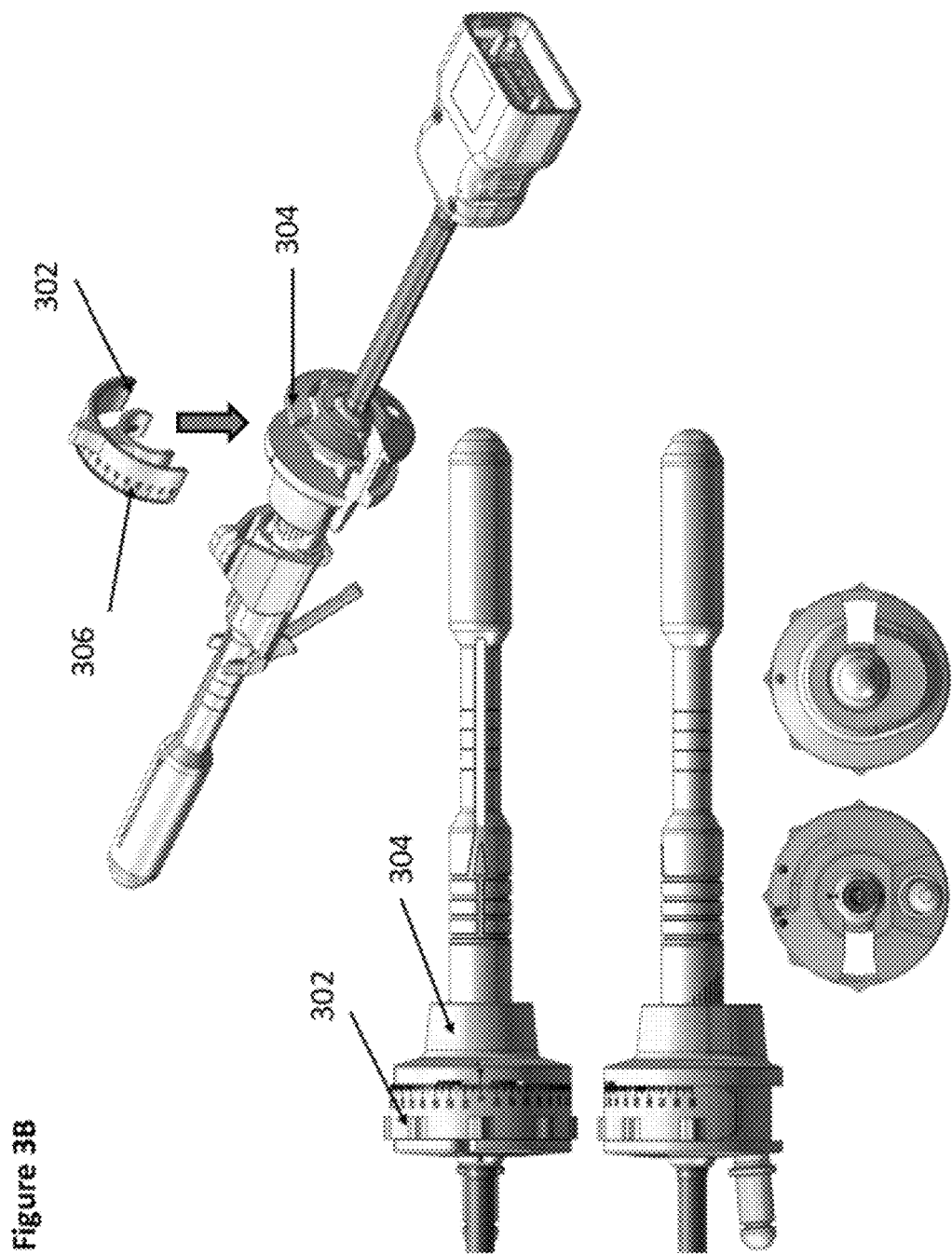
FIG. 3B shows additional views of the rotational adjustment mechanism shown in FIG. 3A.

Referring to FIGS. 3A and 3B, rotation adjustment mechanism 112 is shown, comprising dial 302, hub 304 and rotation scale 306. In the embodiment shown, rotation adjustment mechanism 112 adjusts the rotational position of handle 106 around an axis of rotation that runs through the length of trans-orifice intervention guidance apparatus 100. In use, a user rotates dial 302 in either a clockwise or counterclockwise direction.

Figure 8A:
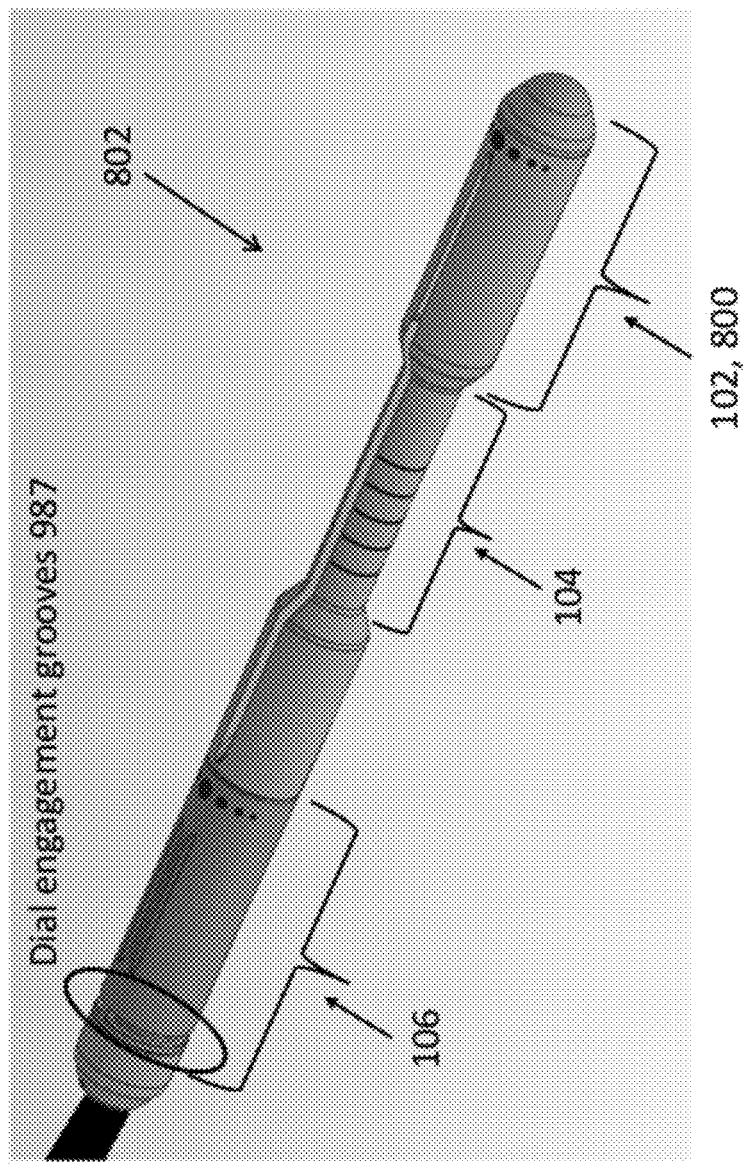
FIG. 8A show a surface view of an embodiment of a trans-orifice apparatus.

In embodiment shown dial 302 is removably engaged to handle section 106, for example by frictional engagement, and a rotation of handle section results. In the embodiment shown, since the handle is connected to the neck and coil sections 104 and 102, a rotation of the handle section results in rotation of the trans-orifice intervention guidance apparatus 100. When dial 302 is rotated, dial 302 can engage grooves 987 in handle section 106 shown in FIG. 8A, which rotates relative to same to stationary hub 304. Rotation scale 306, in the embodiment of FIGS. 3A and 3B, includes a display of discrete rotational positions to inform a user of a rotation applied.

In alternate embodiments, a rotation adjustment mechanism can rotate needle tube, neck and coil sections, while keeping handle section stationary.

Figure 4A:
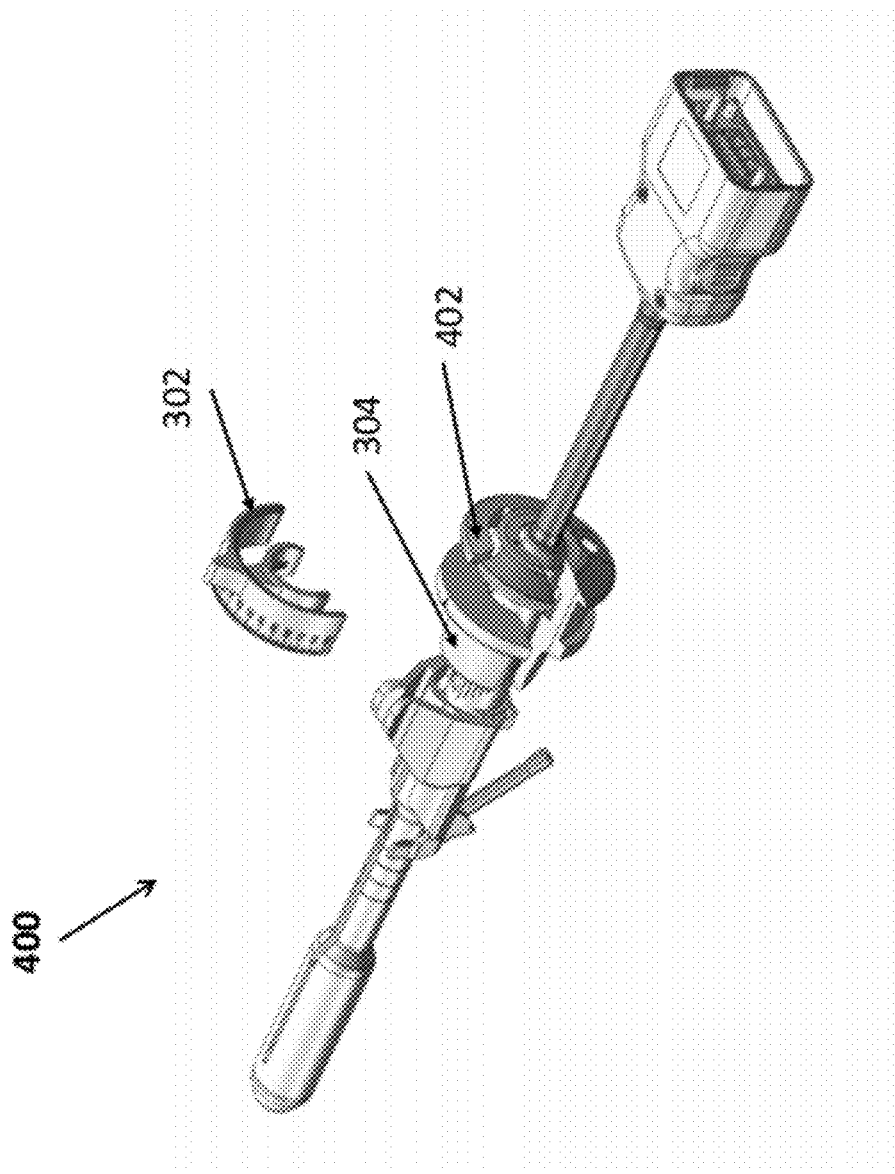

In some embodiments, rotation adjustment mechanism 112 includes a locking mechanism, shown in FIGS. 3 and 4. As shown, the locking mechanism includes detent 402, dial 302 and hub 304. When dial 302 is rotated, detent 402 provides sufficient spring load between hub 304 and dial 302 for self-locking of the rotation mechanism. In the embodiment, dial 302 contains a pin that engages slot on detent 402, which restricts movement past a certain point and prevents over rotation of dial 302.

In embodiments, any "sticking" of detent 402 and hub 304 interfaces can be prevented by coating surfaces with anti stick-slip materials including, but not limited to, polytetrafluoroethylene.

In other embodiments, a rotation adjustment mechanism can be configured for a rotation of 360 degrees. In other embodiments, the total rotation of a rotation adjustment mechanism can be limited to 90 degrees, or 180 degrees.

Figure 8C:
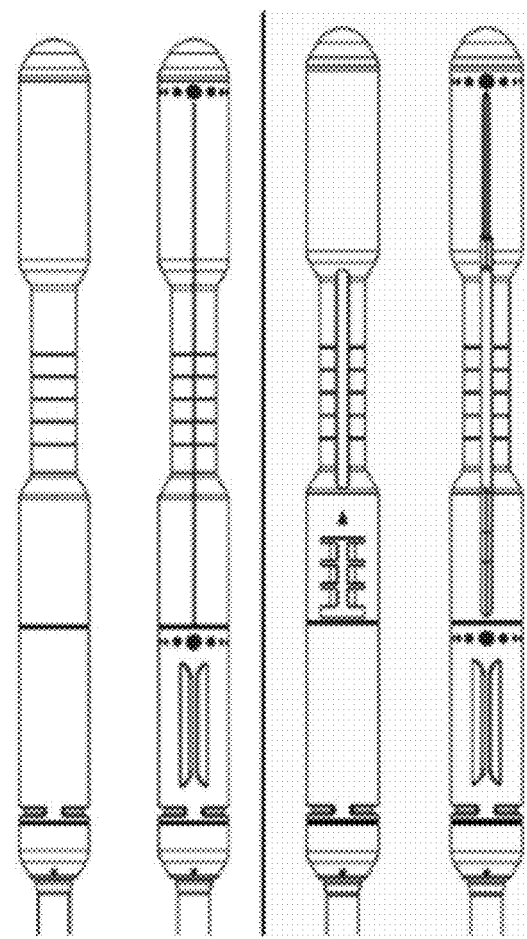
FIG. 8C shows surface views of embodiments of a trans-orifice apparatus.
Figure 9:
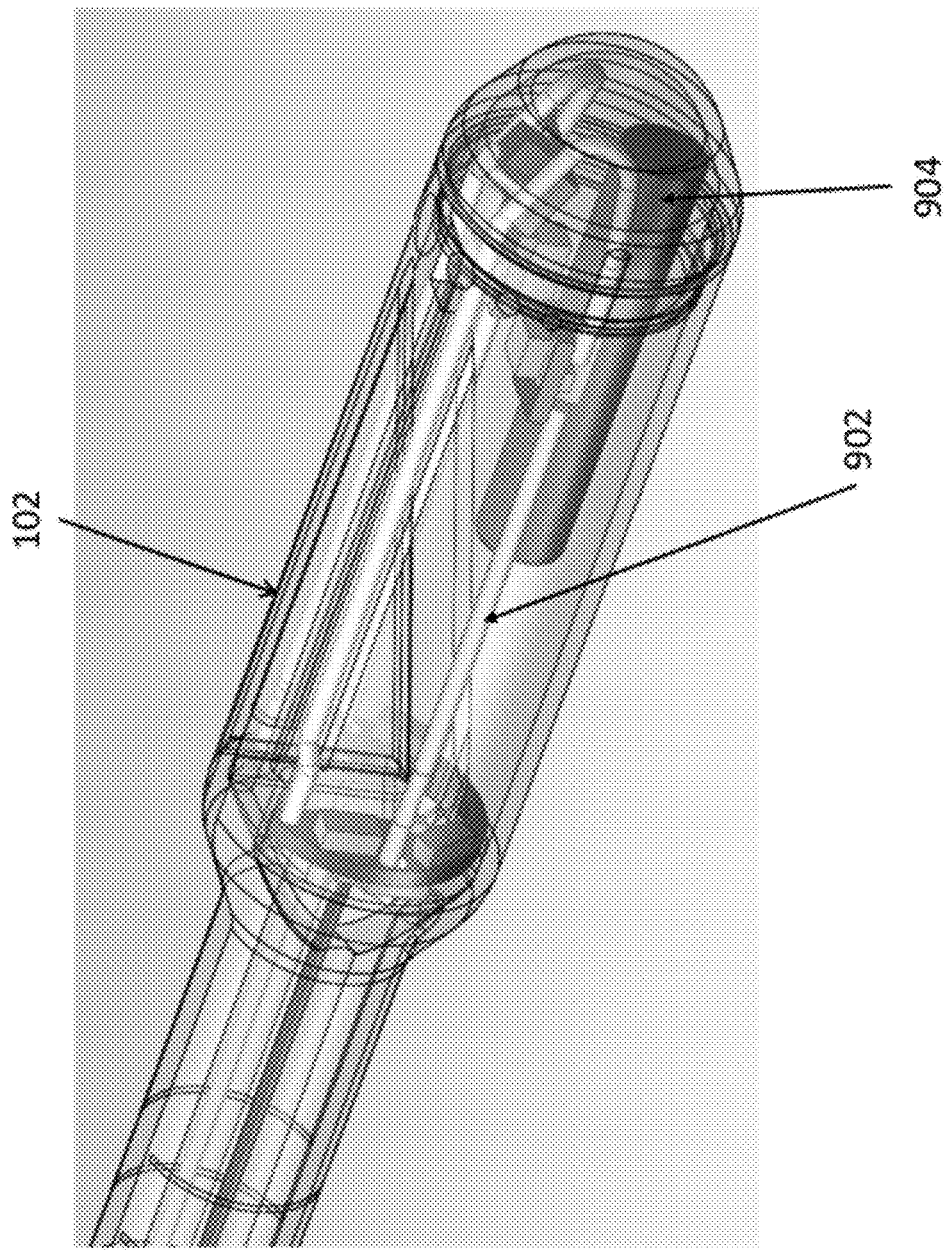
FIG. 9 shows an isometric subsurface view of an embodiment of an imaging component of a trans-orifice guidance apparatus, having a fiducial marker.

Referring to FIGS. 8 and 9, apparatus 802 is shown having head 102 section with imaging component 800, that is connected to circuitry in handle section 106. Imaging component 800 includes imaging coils 902 embedded therein. These imaging coils 902 can be used to obtain MRI images of a tissue of interest in a patient, such as the patient's prostate, when trans-orifice guidance apparatus 100 is in use. The inclusion of imaging coils 902 in trans-orifice guidance apparatus 100 can allow a user to perform image guided biopsy using trans-orifice guidance apparatus 100. FIG. 8C shows alternative embodiments of apparatus 802 without slots for interventional devices. As shown in FIG. 9, in some embodiments, to track the position of trans-orifice guidance apparatus 100, fiducial marker 904, which can be MRI visible, can be maintained within coil section 102 and can be seen on a resulting MRI image. The position of fiducial marker 904 can be used as a reference point when performing image guided intervention.

In use, coil section 102 of trans-orifice guidance apparatus 100 is inserted into a patient's bodily cavity, for example the vagina or the rectum. Following insertion, imaging coils 902 can be used to generate MRI images of the tissue surrounding intra-orifice intervention guidance apparatus 100, to identify target tissue locations. The rotation adjustment mechanism 112 can be used to position imaging coils 902 in various orientations within the cavity of insertion, allowing the user to select their desired field of image. Fiducial marker 904 can be used as a reference point on generated images to facilitate identification of target tissue coordinates. In alternative embodiments, a user may refer to images of the patient's tissue, obtained from previous imaging procedures, to identify target tissue for biopsies and intervention. Target tissues can be identified, for example, by an operator's review of captured images. Alternatively, software detection systems can be used to analyze medical images and identify localized cell regions or areas of interest for intervention.

In addition to imaging capabilities, during interventional procedures, trans-orifice intervention guidance apparatus 100, can additionally be used to guide and position interventional devices such as needles and/or catheters, to a target tissue. A user can insert an interventional device, such as a biopsy needle, catheter or other medical instrument, into needle tube 108, prior to trans-orifice intervention guidance apparatus 100 insertion. In other instances, needles and catheters may be attached to or removed from needle tube 108 after apparatus 100's insertion, by sliding needle tube 108 and neck 104 outside of the patient's body cavity to provide access to needle tube 108. Neck 104 can then be inserted or reinserted into the body cavity, and angle adjustment mechanism 110 and rotation adjustment mechanism 112 can be used to position needle tube 108, and the interventional device inserted in needle tube, for guided and controlled access to target tissues.

In some embodiments, imaging and interventional device positioning can be performed concurrently, or as an iterative process, to ensure that all target tissue locations are accessed by the interventional device, such as the needle, catheter or other medical instrument.

In instances where several biopsies are being performed on a patient, a biopsy can be tracked with coil 902 and magnetic resonance imaging, or other concurrent imaging technology, such as an exterior ultrasound probe that can track the position of the interventional device in the patient. In some embodiments the ultrasound image can be co-registered with the MRI image to assist the user in delivering the interventional device to the target tissue location.

Based on a resulting image, trans-orifice intervention guidance apparatus 100 can be repositioned to improve target tissue contact. Furthermore, in interventional procedures involving several biopsies, trans-orifice guidance apparatus 100 can be repositioned after each biopsy, using imaging and guidance features, without requiring the removal of head 102 from the patient's body.

Figure 10:
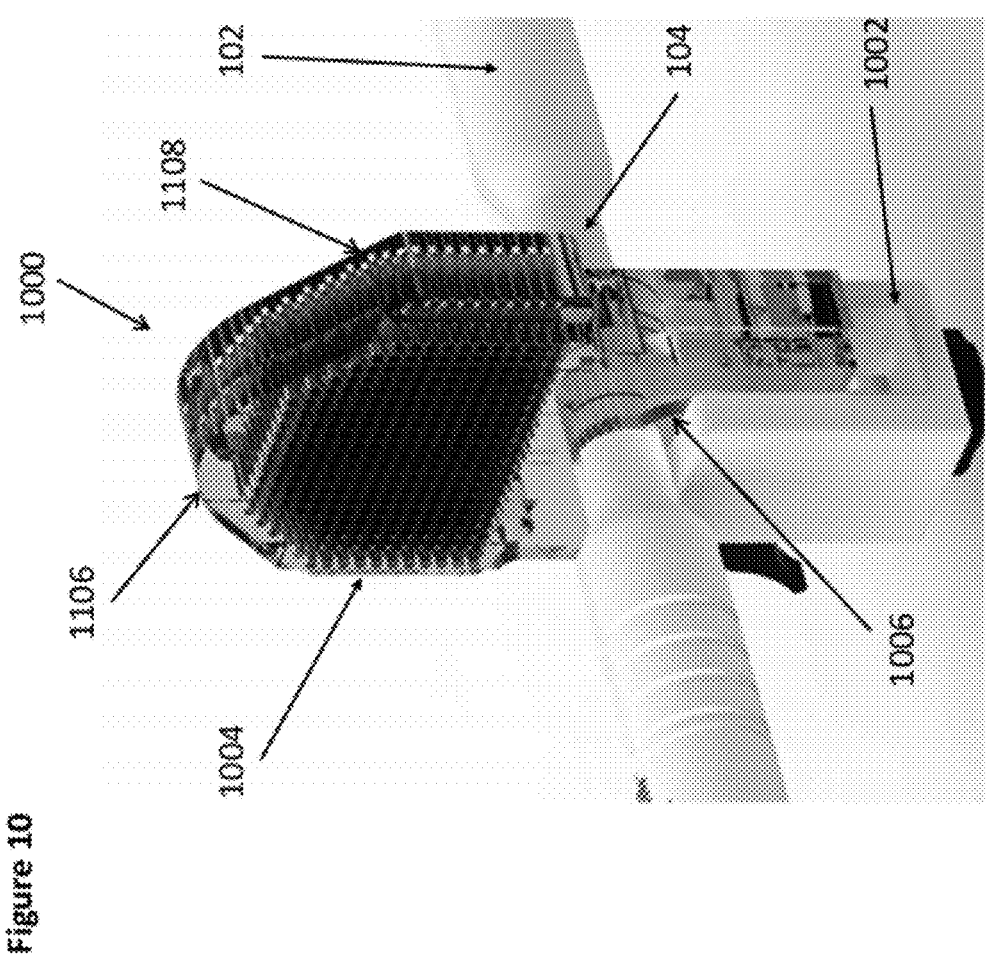
FIG. 10 shows an isometric view of another embodiment of an intervention tool securement and adjustment mechanism.

Referring now to FIG. 10, another embodiment of an intervention tool securement and adjustment mechanism is shown, in a transperineal guidance system 1000, for use in interventional procedures. The embodiment of the mechanism shown may be removably attached to an imaging probe, such as to a neck section of the exemplary apparatus 802 shown in FIG. 8. In other embodiments, system 1000 may be attached to other imaging devices, or other support structures.

In the embodiment shown, transperineal guidance system 1000 comprises lock 1002 and frame 1004. In exemplary operation, apparatus 802 is inserted into frame 1004 where it can be secured with lock 1002 and maintain its position when in use, such as when performing transperineal intervention on a patient. During use, coil section 102 is inserted within an existing orifice of a patient, such as the patient's rectum. Frame 1004 is used to guide interventional components such as needles and catheters or other medical instruments interperineally through a patient's skin, such as in embodiments where a patient's prostate is being imaged, through the skin between the patient's rectum and scrotum.

In the embodiment shown in FIG. 10, frame 1004 is fastened to neck 104 by frictional engagement with coil lock 1002. Neck 104 is inserted through opening 1006 in frame 1004 and secured into place by mechanically reducing the size of opening 1006 by setting lock 1002 to the locked position.

As shown in FIGS. 10 and 11A, in some embodiments, transperineal guidance system 1000 includes needle locking system 1100 which secures interventional devices such as needles, catheters or other medical instruments into needle holes 1110. In the embodiment shown, needle locking system 1100 includes front plate 1106, back plate 1108, needle hole reference scale 1102 and cam 1104. A knob 1112 is also shown as operating with lock 1002.

As shown in the embodiment of FIGS. 10 and 11A, frame 1004 includes a series of needle holes 1110 through which catheters and needles are placed during interventional procedures. Needle hole reference scale 1102 serves as a positioning guide for needle hole locations across the surface of frame 1004. For example, in the embodiment shown, needle hole reference scale 1102 contains an alphabetical scale on one axis and a numerical scale on the other axis, to assist in identifying a spatial location of a particular needle hole across the frame 1004, which in some embodiments can be determined by image analysis software for guiding a user to a specific needle hole 1110 that will provide access to the desired biopsy location in a tissue of interest.

In the embodiment of FIGS. 10 and 11A, cam 1104 can be turned so as to move, front plate 1106 relative to back plate 1108 along a guiding mechanism, such as a rail (not shown), which can provide frictional engagement against an interventional device inserted through a needle hole 1110 of front plate 1106 and back plate 1108, such as a needle, catheter or other medical instrument. In some embodiments, front plate 1106 and back plate 1108 can be offset to reduce shear forces on needles and control locking force on needles of slightly different diameters. An alternative embodiment of a transperineal guidance system is shown in FIG. 11B, having frame 1204.

In some embodiments, a needle locking system can operate with an elastomer plate between front and back plates. As shown in FIGS. 12A and 12B, needle locking system 1100 includes elastomer plate 1202, front plate 1106 and back plate 1108. Elastomer plate 1202 is positioned between front plate 1106 and back plate 1108. In this embodiment, when screw or cam 1104 is rotated, front plate 1106 and back plate 1108 are compressed together, exerting compression forces 1204 on elastomer plate 1202 which deforms elastomer plate 1202 and decreases needle hole 1110 diameter, and thus tending to apply compression force on an interventional device inserted in needle hole 1110 and a frictional engagement is formed to prevent unwanted movement of the interventional device. In some embodiments, elastomer plate can comprise deformable material(s) that is/are biocompatible.

Figure 13A:
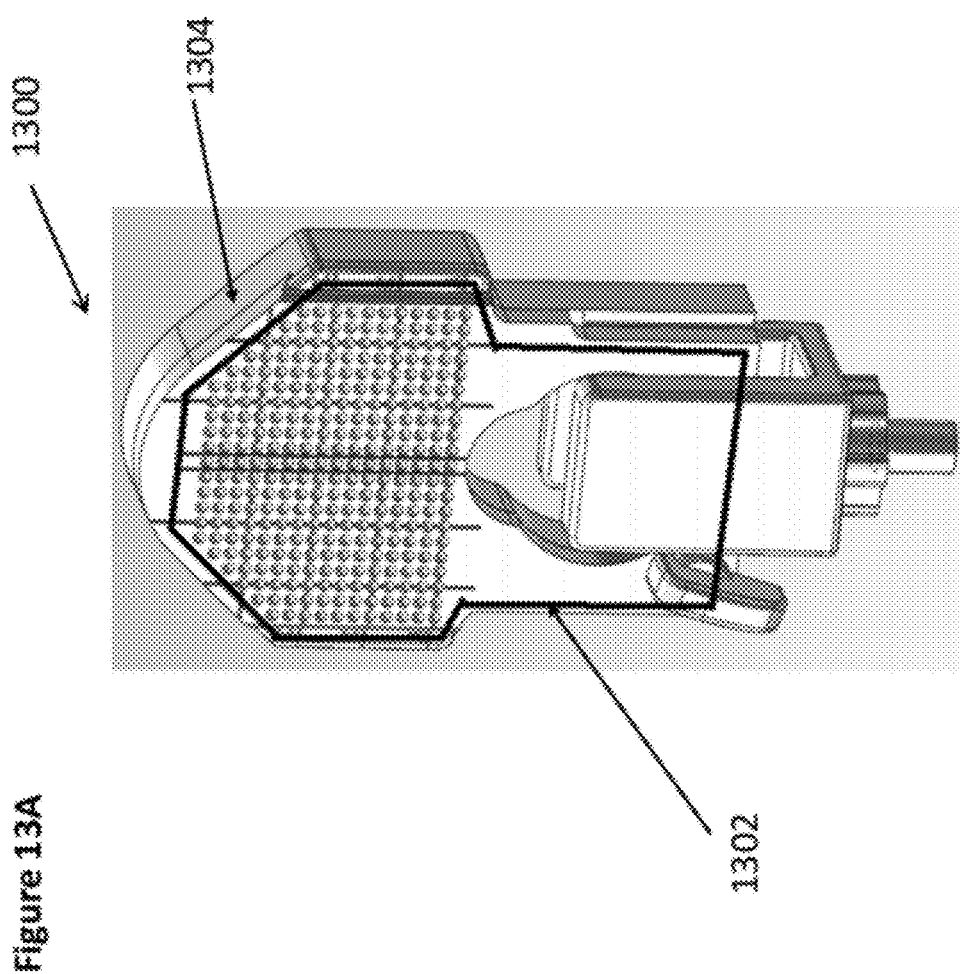
FIG. 13A shows an isometric view of an embodiment of an intervention tool securement and adjustment mechanism including magnetic resonance Imaging single loop coils.
Figure 13B:
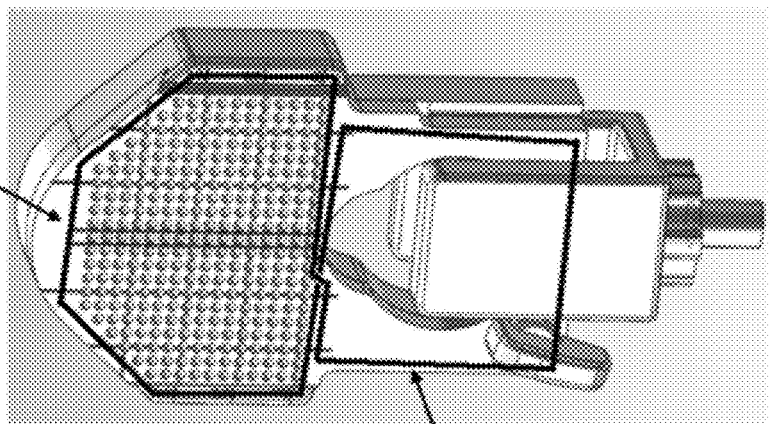
FIGS. 13B and 13C show embodiments of intervention tool securement and adjustment mechanisms including magnetic resonance imaging single loop butterfly coils.
Figure 13C:
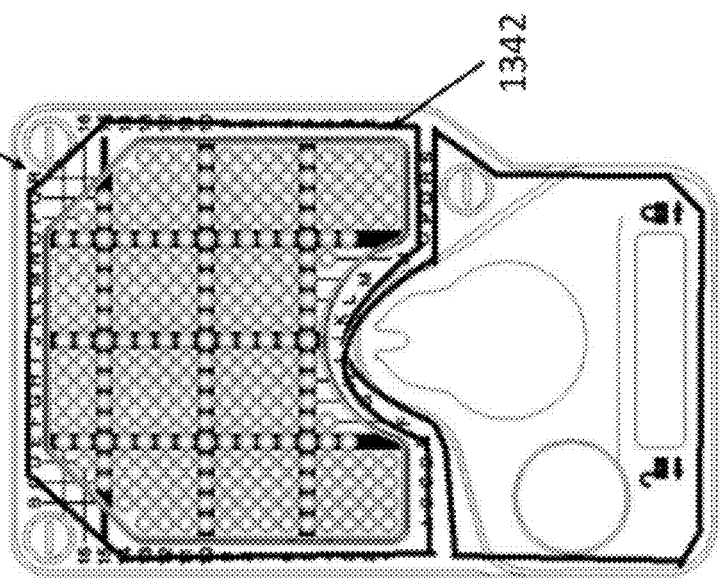

Referring to 13A, 13B and 13C, other embodiments of a transperineal guidance system are shown, which includes magnetic resonance imaging coils embedded in frame 1004. FIG. 13A shows an embodiment of transperineal guidance system 1300 with single loop coil 1302 embedded in frame 1304, which is similar to frame 1004 described above (except for the inclusion of coil 1302 therein). FIG. 13B shows an alternate embodiment of transperineal guidance system 1344 with single loop butterfly coil 1322 embedded in frame 1324. FIG. 13C shows yet another embodiment, of trasnsperineal guidance system 1340 with a single loop butterfly coil 1342 embedded in frame 1344.

The inclusion of a coil, such as coils 1302, 1322 or 1343, in a transperineal guidance system provides enhanced capability for image guided biopsies using the transperineal guidance system. For example, referring to FIG. 13A, single loop coil 1302 can be used to obtain MRI images of a tissue of interest in a patient, such as the patient's prostate, when transperineal guidance system 1000 is in use. In such embodiments, the coil embedded within a frame of the guidance system can be used to provide MRI imaging in lieu of, or in addition to, the apparatus to which the system is attached to (such as, for example, the imaging components 800 of apparatus 802 shown in FIG. 8). During interventional procedures, for example coil section 102 of apparatus 800 may be inserted into a patient's bodily cavity, for example the vagina or the rectum. A frame, as described herein, can be affixed to neck 104 using a coil lock mechanism. In some embodiments coils 1302, 1322 or 1343, and/or coil section 102, can be used to identify target tissue locations. In alternative embodiments, a user may refer to images of the patient's tissue, obtained from previous imaging procedures, to identify target tissue for biopsies and intervention. Target tissues in both instances can be identified, for example, by operator measurements and analysis of images, or by software generated results.

Figure 13D:
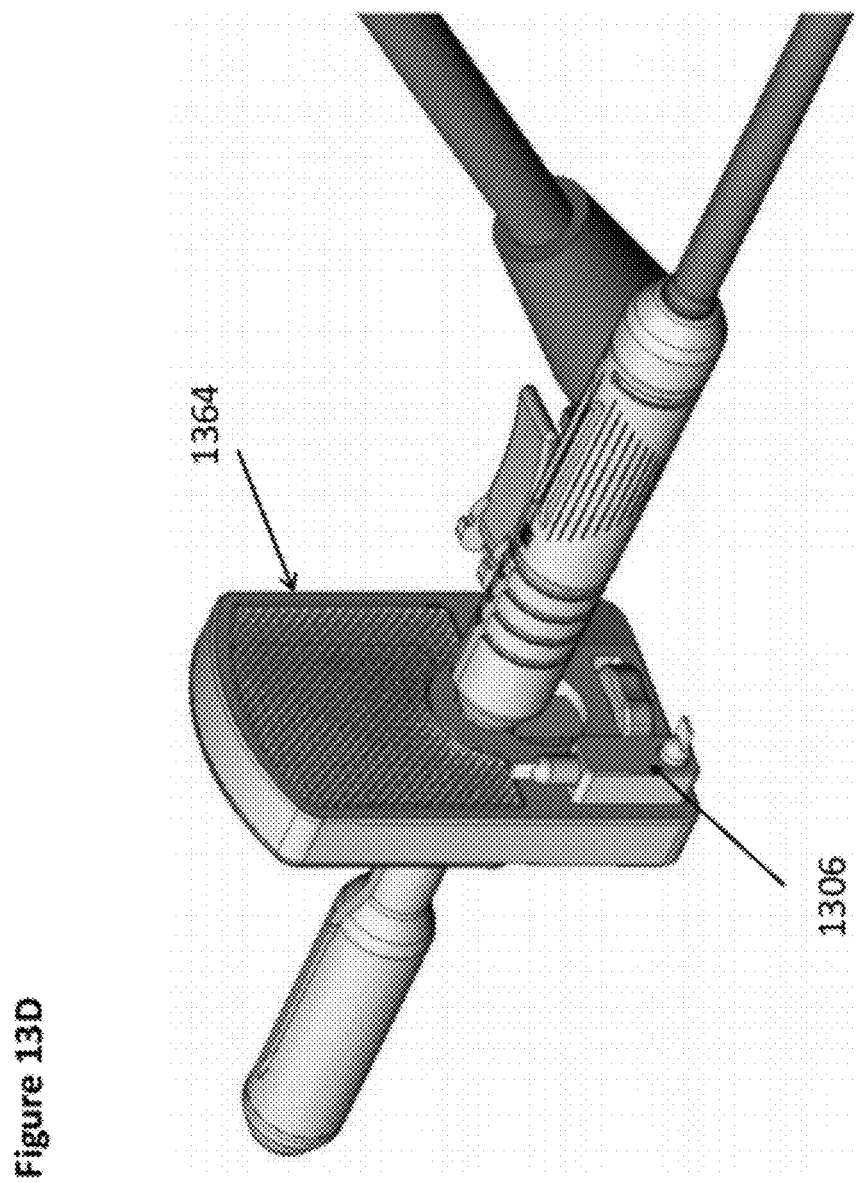
FIG. 13D shows an isometric view of an embodiment of an intervention tool securement and adjustment mechanism including fiducial marker for imaging purposes.

FIG. 13D shows another embodiment of a transperineal guidance system, which includes fiducial marker 1306, which can be MRI visible, and can be positioned on frame 1364 (which is similar to frames 1004, 1154, 1304, 1324 and 1344 described above), such that it can be seen on a resulting MRI image. The position of fiducial marker 1306 can be used as a reference point when performing image guided intervention.

With reference to FIG. 14A, in some embodiments, template 1402 which can be provided and used as a reference guide for needle locations during interventional procedures using the described guidance systems. FIG. 14A shows template 1404, to assist in planning of interventional procedures. This embodiment can be useful, for example, where previous patient images are available to identify target tissue locations or when the computer image with the targets is not close enough to the patient to be able to target the intervention while looking at this image. As shown, template, or label, 1404 may be marked at marked locations 1406 that corresponds to an intervention being planned, and then template 1404 may be applied to a frame, such as frame 1154, for use in a guidance system.

In the embodiment shown, label 1404 contains a pattern of markers 1406 corresponding to needle holes 1152 on frame 1154. Prior to interventional procedure, an operator can identify specific needle holes 1152 on frame 1004 to be used in the interventional procedure, and can mark label 1404 accordingly with location markers 1406. Label 1404 can be marked, for example, by shading marker pattern using a printer or by hand. In some embodiments, once label 1404 has been marked, it can be affixed directly to frame 1154.

Figure 14C:
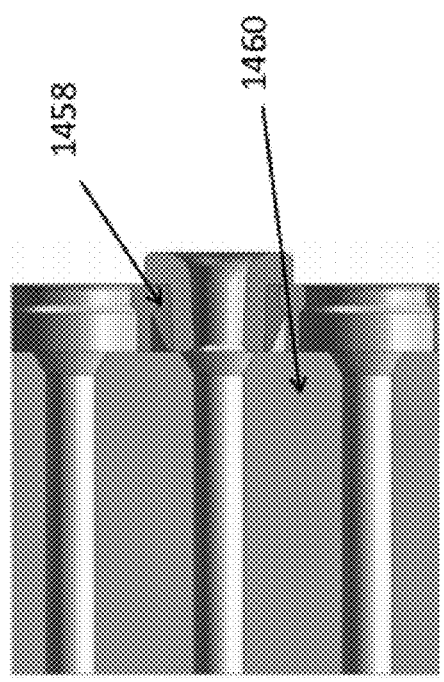
FIGS. 14B and 14C show a template to identify specific needle holes in an intervention tool securement and adjustment mechanism.
Figure 14B:
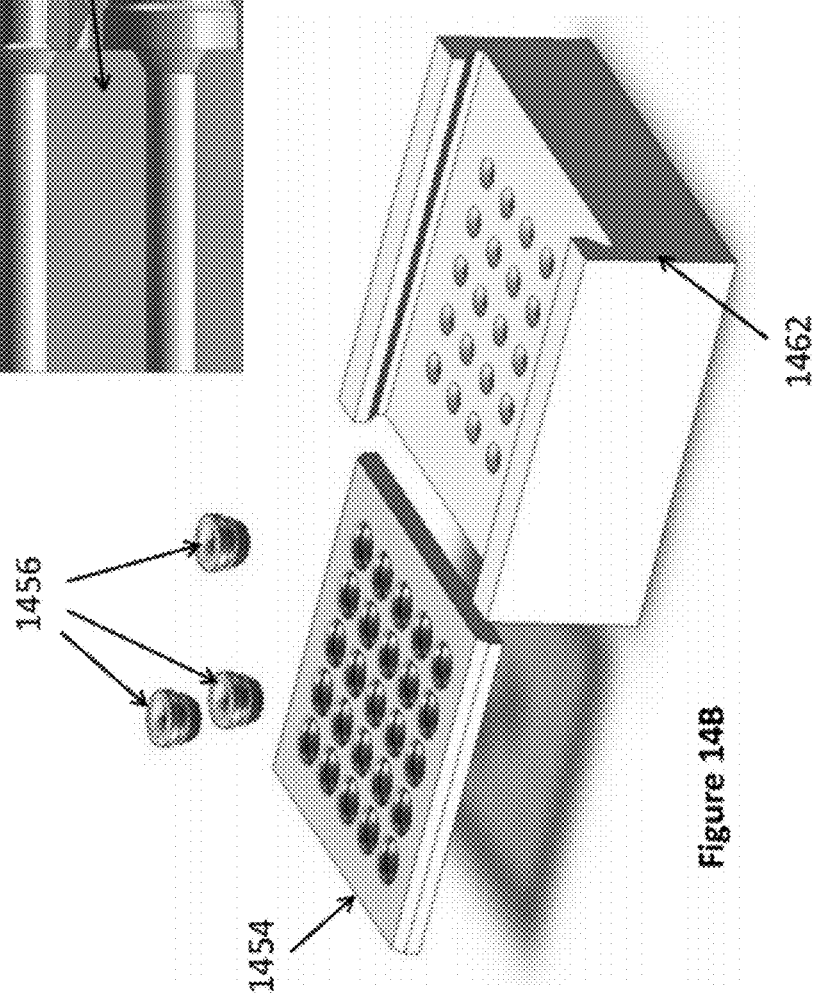

In FIG. 14B, an alternate embodiment having template 1454 and markers 1456 is shown. As shown, marker 1456 can be inserted onto template 1454 to mark locations for intervention. Template 1454 can then be placed onto a frame (a portion of which is shown in FIG. 14B as 1462) and secured in place, for use in guiding interventional procedures. In some embodiments, marker 1456 may include a hard plastic guide that doubles as a marker, and also having an elastomeric ring 1458 for engaging with template 1460, as shown in FIG. 14C.

In some embodiments, a needle depth sensor can be integrated into template 1404 or 1460 to provide feedback on needle depth. In some embodiments, the needle depth sensor can be a small tubular device that can be plugged into needle holes, such as holes 1110 or 1152 (or in the case of marker 1456, integrated with marker 1456) for measuring the distance the interventional device, such as a biopsy needle, catheter or other medical instrument has passed through needle holes by way of either optical or mechanical position encoding. In embodiments using optical encoding, interventional devices can be marked with equally spaced markings and light emitter and light receiver technology can be housed inside needle hole (such as 1110. or 1152). In an embodiment, the light emitter and receive can operate to count the number of markings that have passed through the needle hole, and calculate the corresponding depth that the interventional device has traveled based on the known distance between the marker spacings. In embodiments that use mechanical position encoding, a mechanical component can, for example, press a spherical roller or ball against the interventional device as it is being inserted through needle holes. Such an embodiment can be used to count the number of turns of the roller or ball, and calculate the depth that the interventional device has traveled. In some embodiments, an audio or visual signal can be used to alert a user when the depth of the interventional device has reached a desired depth, such as when it has reached the target location in the tissue of the patient.

Figure 14D:
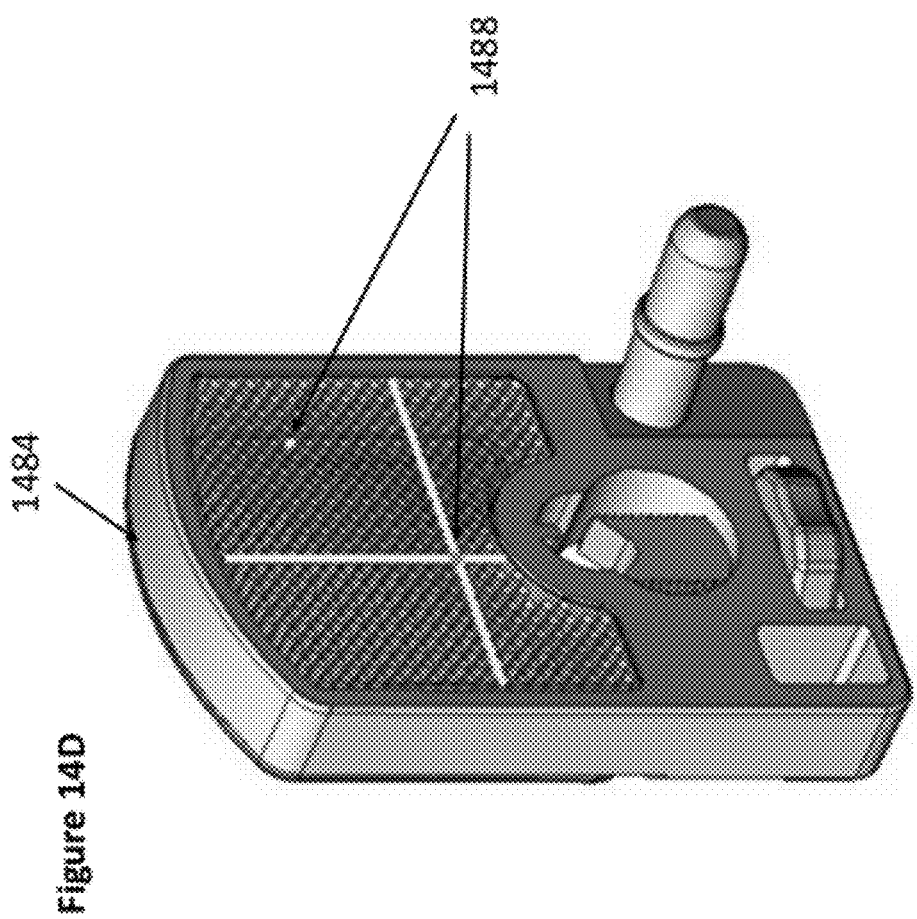
FIG. 14D shows an isometric view of an LED grid to identify specific needle holes in transperineal intervention guidance system.

In the embodiment shown in FIG. 14D an exemplary frame 1484 is shown with Light Emitting Diodes (LEDs) 1488 and embedded programmable chip (not shown). The programmable chip is programmed to activate LEDs during interventional procedures, corresponding to particular needle hole (such as holes 1110) locations on the reference grid where needle insertion should be made. In alternate embodiments, LEDs can be located around two axis' of the frame to create a two dimensional reference grid. In some embodiments, needle insertion locations can be pre-planned using patient images to identify target tissue locations.

Figure 15A:
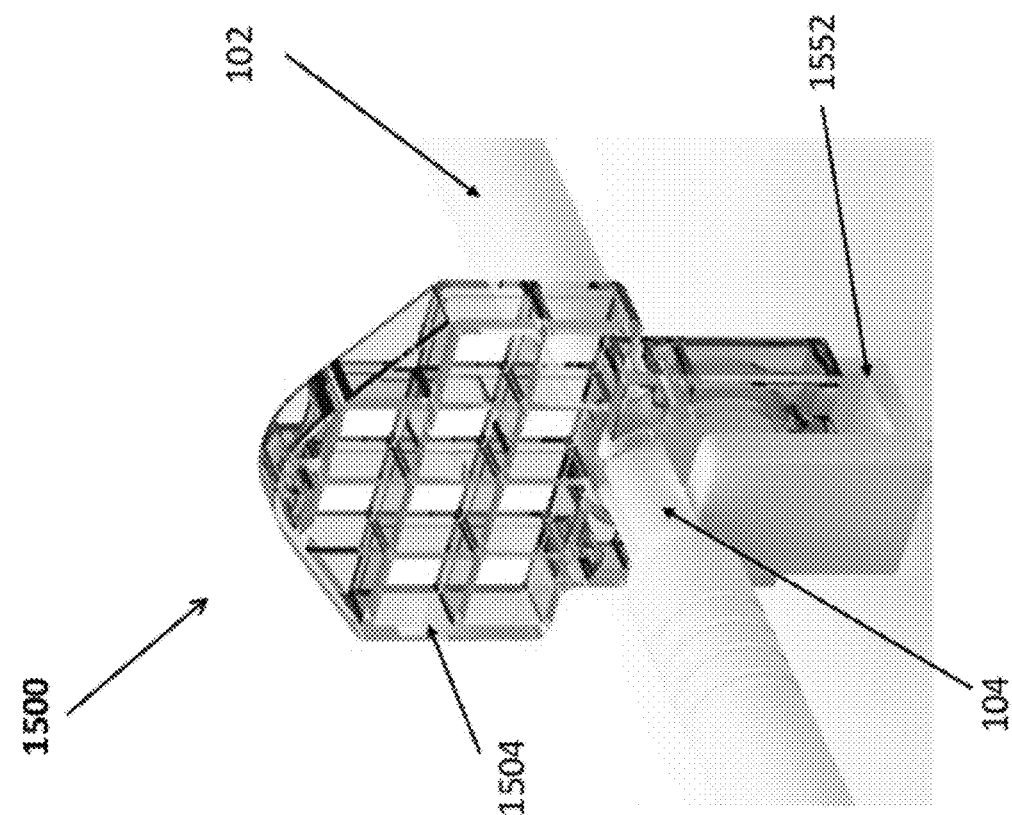
FIG. 15A shows an embodiment of an intervention tool securement and adjustment mechanism with an angle template system.

With reference to FIGS. 15A, 15B and 15C, an alternate embodiment of transperineal guidance system 1500 is shown, having a needle angle adaptor comprised of angle plug 1502 and frame 1504. Angle plug 1502, shown in FIG. 15C, comprises angle scale 1506, angle lock 1508 and intervention device holder 1510. Frame 1504, includes template apertures 1512 to receive, for example, angle plug 1502. In the embodiment shown, angle plug 1502 can be secured to frame, or angle template, 1504 by a portion of plug 1502 to a selected template aperture 1512. By engaging angle lock 1508, device holder 1510 can also be secured at a particular position of angle plug 1502, which is secured on frame 1504. The angle of engagement between frame 1504 and device holder 1510 can be adjusted and locked into place by angle lock 1508 which affixes angle plug 1502 onto frame 1504 at a particular angle to restrict the angular entrance of intervention instruments, such as needles, that are secured to device holder 1510, such as shown in FIG. 15D. Such embodiments tends to allow for off axis needle insertions which may be required during interventional procedures to negate pubic arch interference, necessary for example, with patients having large prostates. Embodiments of angle plugs, their interaction with template apertures, and intervention devices suitable for use therewith, are described in more detail in U.S. patent application Ser. No. 12/822,110, filed Jun. 23, 2010, the contents of which are herein incorporated by reference.

Figure 16:
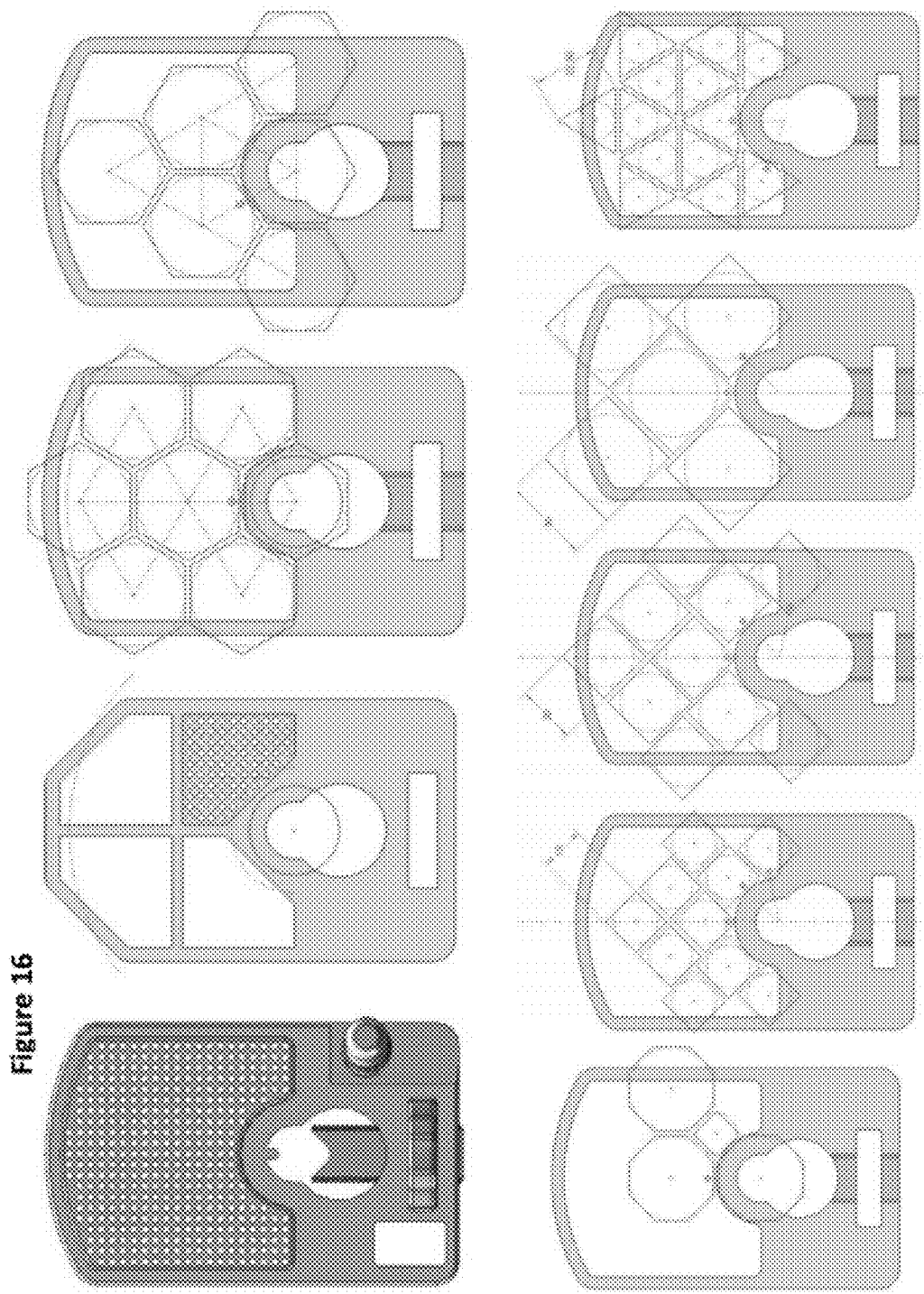
FIG. 16 shows alternate embodiments of guidance system.

In FIG. 16, alternate configurations of transperineal grids, and needle block shapes and positions, for alternate embodiments for a frame of a transperineal guidance system are shown.

In some embodiments, imaging and intervention can be performed concurrently or as an iterative process, to ensure that all target tissue locations are accessed by the interventional device, such as the needle, catheter or other medical instrument. In instances where several biopsies are being performed on a patient, a biopsy can be tracked with image guidance technology, and adjustments to needle locations and angles can be made for subsequent biopsies, without requiring the removal of coil section 102 of apparatus 800 from the patient's orifice or body cavity.

The present invention has been described with regard to specific embodiments. The scope of the claims should not be limited by the preferred embodiments set forth in the examples, but should be given the broadest interpretation consistent with the description as a whole. It will be obvious to persons skilled in the art that a number of variants and modifications can be made without departing from the scope of the invention as described herein.

The invention claimed is:

1. An intervention apparatus comprising:
    a probe having an orifice insertion portion, the orifice insertion portion being configured for insertion into an orifice of a patient during a magnetic resonance imaging guided biopsy;
    a neck portion that connects the orifice insertion portion; and
    a handle portion that connects to the neck portion;
    wherein a cross-section diameter of the neck portion is smaller than a cross-section diameter of the orifice insertion portion, to provide additional patient comfort when the orifice insertion portion is inserted entirely within the orifice of the patient;
    a needle tube that accommodates a needle of an intervention tool; and
    an intervention tool securement and adjustment mechanism that controls a location of the intervention tool securement and adjustment mechanism on the neck portion, and controls an angle of the needle tube relative to the neck portion;
    wherein the securement and adjustment mechanism includes a saddle situated on an exterior surface of the neck portion, the saddle being configured to be selectively movable along the neck portion to adjust and secure the location of the intervention tool securement and adjustment mechanism on the neck portion at any of a variety of selectable locations along the neck portion, and
    wherein the securement and adjustment mechanism includes an angle adjustment mechanism that is configured to be selectively movable along the saddle to adjust and secure the angle of the needle tube at any of a variety of selectable angles relative to the neck portion.

2. The apparatus of claim 1, wherein the orifice insertion portion includes an imaging coil configured for use with magnetic resonance imaging (MRI) of a tissue of interest in the patient.

3. The apparatus of claim 2, wherein the MRI of the tissue of interest provides guidance of the intervention tool to the tissue of interest.

4. The apparatus of claim 1, wherein the angle adjustment mechanism includes a locking mechanism to maintain the angle of insertion of the intervention tool.

5. The apparatus of claim 4, wherein the orifice insertion portion of the probe includes a longitudinal axis and a channel therethrough, and the angle adjustment mechanism directs the intervention tool through the channel towards the tissue of interest.

6. The apparatus of claim 5, further comprising a rotational adjustment mechanism removably attached to the probe and operable to rotate the probe around the longitudinal axis, whereby the angle adjustment mechanism is also rotated around the longitudinal axis.

7. The apparatus of claim 6, wherein the intervention tool securement and adjustment mechanism, the rotational adjustment mechanism and the channel of the orifice insertion portion are configured so that, when the orifice insertion portion of the probe is inserted through the anus of the patient and positioned in the rectum, the intervention tool is delivered through the channel inter-orifice through the wall of the rectum to the tissue of interest.

8. The apparatus of claim 1, wherein the orifice insertion portion and the neck portion are substantially cylindrical.

9. The apparatus of claim 1, wherein the intervention tool securement and adjustment mechanism includes an intervention tool locking mechanism thereon, to secure the intervention tool in a desired location on the neck portion.

10. The apparatus of claim 9, wherein the intervention tool securement and adjustment mechanism is configured so that, when the orifice insertion portion of the probe is inserted through the anus of the patient, the intervention tool is delivered transperineally to the tissue of interest.

11. The apparatus of claim 10, wherein the intervention tool securement and adjustment mechanism further comprises a second imaging coil configured for use with MRI of the tissue of interest in the patient.

12. The apparatus of claim 10, wherein the angle adjustment mechanism is removably attached to the intervention tool securement and adjustment mechanism.

13. The apparatus of claim 1, wherein the securement and adjustment mechanism includes a slider that is configured to be selectively movable along the saddle to adjust the angle of the needle tube.

14. The apparatus of claim 1, wherein the orifice insertion portion comprises a generally non-rigid exterior structure.

15. The apparatus of claim 1, wherein the smaller cross-section diameter of the neck portion enables the patient's orifice to close around the neck portion to provide additional securement of the apparatus when in use.

16. The apparatus of claim 1, wherein at least a section of the neck portion adjacent the orifice insertion portion is not covered by the intervention tool securement adjustment mechanism, thereby exposing the smaller cross-section diameter of the neck portion adjacent the orifice insertion portion.

\* \* \* \* \*